US007989089B2

(12) United States Patent
Wang et al.

(10) Patent No.: US 7,989,089 B2
(45) Date of Patent: Aug. 2, 2011

(54) ORGANIC LUMINESCENT COMPOUNDS AND METHODS OF MAKING AND USING SAME

(75) Inventors: Suning Wang, Kingston (CA); Ruiyao Wang, Kingston (CA)

(73) Assignee: LG Display Co., Ltd., Seoul (KR)

( * ) Notice: Subject to any disclaimer, the term of this patent is extended or adjusted under 35 U.S.C. 154(b) by 1805 days.

(21) Appl. No.: 10/825,685

(22) Filed: Apr. 16, 2004

(65) Prior Publication Data

US 2004/0265628 A1 Dec. 30, 2004

Related U.S. Application Data

(60) Provisional application No. 60/463,337, filed on Apr. 17, 2003.

(30) Foreign Application Priority Data

Apr. 17, 2003 (CA) .................................. 2425819

(51) Int. Cl.
*H01L 51/54* (2006.01)
*C09K 11/06* (2006.01)
*C07D 487/22* (2006.01)
(52) U.S. Cl. ........ 428/690; 428/917; 313/504; 313/506; 257/E51.05; 546/64; 546/77; 548/301.7; 252/301.16; 252/301.35
(58) Field of Classification Search ............... 546/64
See application file for complete search history.

(56) References Cited

U.S. PATENT DOCUMENTS

| 5,281,489 A * | 1/1994 | Mori et al. ..................... 428/690 |
| 6,312,835 B1 | 11/2001 | Wang et al. .................... 428/690 |
| 6,500,569 B2 | 12/2002 | Wang et al. .................... 428/690 |
| 7,291,404 B2 * | 11/2007 | Aziz et al. ..................... 428/690 |
| 2004/0209117 A1 * | 10/2004 | Aziz et al. ..................... 428/690 |
| 2004/0234809 A1 | 11/2004 | Chen et al. |

FOREIGN PATENT DOCUMENTS

| CN | 1289774 A | 4/2001 |
| JP | 2001-23777 * | 1/2001 |

OTHER PUBLICATIONS

Machine translation of JP 2001-23777.*
Wu et al., "Synthesis and spectroscopic DNA binding studies of homoleptic and heteroleptic ruthenium (II) complexes with imidazo[4,5-f][1,10]phenanthroline or its derivatives", Transition Met. Chem., 24, pp. 299-303 (1999).*
Zhang et al., "Effect of intramolecular hydrogen-bond on the DNA-binding and photocleavage properties of polypyridyl cobalt (III) complexes", Inorganica Chimica Acta, 339, pp. 34-40 (2002).*
Rui-Yao Wang et al., "1-Methyl-2-(anthryl)-imidazo[4,5-f][1,10]-phenanthroline . . . for Electroluminescent Devices", Advanced Functional Materials, vol. 15, pp. 1483-1487 (2005).*
Bian, Z.-Q., et al., "Study on the Electroluminescent Properties of Some Ternary Europium Complexes with Phenanthroline Derivatives as the Neutral Ligands," Science in China (series B) (Chinese version), (2004) 34:113-120.
Bian, Z.-Q., et al., "Syntheses, Spectroscopic and Crystal Structural Studies of Novel Imidazo[4,5-f]1,10-phenanthroline derivatives and their Eu(III) Ternary Complexes with Dibenzoylmethane," Polyhedron (2002) 21:313-319.
Bian, Z.-Q., et al., "A Novel Ternary Complex of Europium (III) for Electroluminescent Device," Chemical Research in Chinese Universities, (2002) 18(4): 466-468.
Guan, M. et al., "Bright Red Light-Emitting Electroluminescence Devices Based on a Functionalized Europium Complex," New J. Chem, (2003) 27: 1737-1734.
Jia, W.-L., et al., "Blue Luminscent Three-Coordinate Organboron Compounds with 2,2,'-Dipyridylamino Functional Group," J. Org. Chem. (2003) 68: 701-705.
Kido, J. et al., "Organo Lanthanide Metal Complexes for Electroluminescent Materials," Chem. Rev., (2002) 102: 2357-2368.
Koene, B., et al., "Asymmetric Triaryldiamines as Thermally Stable Hole Transporting Layers or Organic Light-Emitting Devices," Chem. Mater. (1998) 10(8): 2235-2250.
Liang, F., et al., "Oxadiazole-Functionalized Europium(III) β-Diketonate Complex for Efficient Red Electroluminescence," Chem. Mater. (2003) 15(10): 1935-1937.
Liu, S.-F., et al., "Syntheses, Structures, and Electroluminescence of New Blue/Green Luminescent Chelate Compounds: Zn(2-py-in)$_2$(THF), BPh$_2$(2-py-in), Be(2-py-in)$_2$ and BPh$_2$(2-py-aza) [2-py-in =2-(2-pyridyl)indole; 2-py-aza =2-(2-pyridyl)-7-azaindole]," J. Am. Chem. Soc. (2000) 122: 3671-3678.
Pang, J. et al., "Syntheses, Structures, and Electroluminescence of New Blue Luminescent Star-Shaped Compounds Based on 1,3,5-Triazine and 1,3,5-Trisubstituted Benzene," J. Mater. Chem., (2002) 12: 206-212.

(Continued)

Primary Examiner — Marie R. Yamnitzky
(74) Attorney, Agent, or Firm — McKenna Long & Aldridge LLP

(57) ABSTRACT

The invention provides organic compounds of the general structure (1)

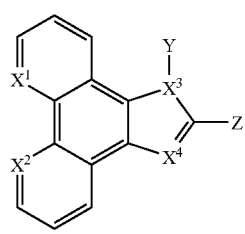

(1)

that are photoluminescent and electroluminescent, emitting intense blue light. The invention further provides methods of synthesizing such compounds, methods of producing photoluminescence and electroluminescence, methods of applying the compounds in thin films, and uses of the compounds of the invention in luminescent probes, electroluminescent displays and as pH probes and metal ion detectors.

29 Claims, 15 Drawing Sheets

OTHER PUBLICATIONS

Shirota, Y. "Organic Materials for Electronic and Optoelectronic Devices," *J. Mater. Chem.*, (2000) 10: 1-25.

Sun, M., et al., "Bright and Monchromic Red Light-Emitting Electroluminescence Devices Based on a New Multifunctional Europium Complexe," *Chem. Commun.* (2003) 702-703.

Wu, Q., et al., "Novel Blue Luminescent/Electroluminescent 7-Azaindole Derivatives: 1,3-Di(N-7-azaindolyl)benzene, 1-Bromo-3,5-Di(N-7-azaindolyl)benzene, 1,3,5-Tri(N-7-azaindolyl)benzene, and 4,4'-Di(N-7-azaindolyl)biphenyl," *Chem. Mater.* (2001) 13(1): 71-77.

Xin, H., et al., "Photoluminescence and Electroluminescence Properties of Three Ternary Lutetium Complexes," *New J. Chem.* (2003) 27:1485-1489.

Yamazaki, S. "Chromium(VI) Oxide-Catalyzed Oxidation of Arenes with Periodic Acid," *Tetrahedron Letters* (2001) 42: 3355-3357.

Yang, W.-Y., et al., "Syntheses, Structures, and Luminescence of Novel Lanthanide Complexes of Tripyridylamine, N,N,N',N'-Tetra(2-pyridyl)-1,4-phenylenediamine and N,N,N',N'-Tetra(2-pyridyl)-biphenyl-4-4'-diamine," *Inorg. Chem.* (2001) 40: 507-515.

\* cited by examiner

ORGANIC LUMINESCENT COMPOUNDS AND METHODS OF MAKING AND USING SAME

This application claims the benefit of priority from U.S. Provisional Application Ser. No. 60/463,337, filed Apr. 17, 2003, which is herein incorporated by reference in its entirety.

FIELD OF THE INVENTION

The invention relates to organic compounds having luminescent properties, and to methods of synthesizing and using such compounds. The invention more particularly relates to compounds having photoluminescent and/or electroluminescent properties, and to synthesis and uses of same. The invention also relates to compounds having photo-receptor properties due to their ability to separate charges. The invention also relates to compounds having photon harvesting properties. The invention also relates to compounds that visibly display detection of metal ions or acid. The invention further relates to compounds that can provide a molecular switch.

BACKGROUND OF THE INVENTION

Production of devices based on electroluminescent display is a rapidly growing, billion dollar industry. Bright and efficient organic light-emitting diode (OLED) devices and electroluminescent (EL) devices have attracted considerable interest due to their potential application for flat panel displays (e.g., television and computer monitors). OLED based displays offer advantages over the traditional liquid crystal displays, such as: wide viewing angle, fast response, lower power consumption, and lower cost. However, several challenges still must be addressed before OLEDs become truly affordable and attractive replacements for liquid crystal based displays. To realize full color display applications, it is essential to have the three fundamental colors of red, green, and blue provided by emitters with sufficient color purity and sufficiently high emission efficiency.

In general, when a potential is applied across an OLED, holes are said to be injected from an anode into a hole transporting layer (HTL) while electrons are injected from a cathode into an electron transporting layer (ETL). The holes and electrons migrate to an ETL/HTL interface. Materials for these transporting layers are chosen so that holes are preferentially transported by the HTL, and electrons are preferentially transported by the ETL. At the ETL/HTL interface, the holes and electrons recombine to give excited molecules which radiatively relax, producing an EL emission that can range from blue to near-infrared (Koene, 1998).

In providing one of the key color components for electroluminescent display devices, blue luminescent compounds are among the most sought-after materials by industry around the world. Two alternative ways in which blue luminescence can be achieved are: (1) providing a molecule which emits blue color (emitter), and (2) doping an emitter such that the combination yields blue luminescence. Conveniently, the emitter can be an inorganic metal ion such as, for example, lanthanide, which emits blue light via d to f or f to f electronic transitions, or an organic molecule which has conjugated $\pi$ bonds and emits blue light via $\pi$ to $\pi$ or $\pi$ to n electronic transitions.

A common problem with blue emitters is their lack of long term stability in OLEDs. OLEDs generally suffer from a gradual intensity decrease of the blue hue, which results in gradual deterioration of the color purity of the display, and ultimately failure of the device. Television and computer monitors must perform consistently for at least five years in order to be commercially feasible. Even this modest expectation is a big challenge for currently available OLEDs.

There are several blue luminescent inorganic coordination compounds known (U.S. Pat. No. 6,500,569, U.S. Pat. No. 6,312,835, Yang, 2001, Jia et al., 2003); however, in some cases, due to a propensity for oxidation and/or hydrolysis reactions, such complexes are not very stable in solution. One family of known inorganic blue emitters, lanthanide ions, have low emission efficiency and require the use of a host (generally an inorganic salt), which makes it difficult to process them into thin films.

Thus, blue luminescent materials that are organic in nature are desirable due to their increased stability, solubility and ability to form thin films. A number of organic blue emitters are known to date (Shirota, 2000, Yang, 2001, Wu et al., 2001, and Liu et al., 2000). Many of these have poor luminescence efficiency and poor stability. Some are luminescent polymers that are difficult to apply in films using chemical vapor deposition (CVD) or vacuum deposition, processes known to produce superior films for electroluminescent displays. Even the best blue emitters currently available do not have the long term stability desired for commercial devices.

The limitations discussed above could restrict the market for OLED products, despite their many superior aspects as compared with liquid crystal displays. Therefore, in order for OLEDs to become truly feasible, there is a need for stable, organic emitters.

BRIEF STATEMENT OF THE INVENTION

In a first aspect, the invention provides a compound having a formula (1)

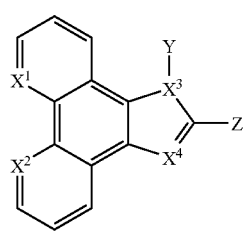

(1)

where $X^1$, $X^2$, $X^3$ and $X^4$ are each independently selected from the group consisting of carbon and nitrogen; Y is selected from the group consisting of hydrogen, a substituted or unsubstituted aryl group, and a substituted or unsubstituted aliphatic group having 1-24 carbon atoms which may be straight, branched or cyclic; Z is a substituted or unsubstituted aryl moiety selected from the group consisting of phenyl, biphenyl, naphthyl, anthryl, phenanthryl, pyrenyl, pyridyl, bipyridyl, indyl, and quinolinyl; and wherein a said substituent is selected from the group consisting of an aryl group, an alkoxy group, a hydroxy group, a halo group, an amino group, a nitro group, a nitrile group, —$CF_3$ and an aliphatic group having 1-24 carbon atoms which may be straight, branched or cyclic. The compound is preferably photoluminescent or electroluminescent.

$X^1$, $X^2$, $X^3$ and $X^4$ may be independently selected from the group consisting of a substituted carbon, an unsubstituted carbon and an unsubstituted nitrogen. In some embodiments, at least one of $X^1$, $X^2$, $X^3$ and $X^4$ may be nitrogen. In some embodiments, all of $X^1$, $X^2$, $X^3$ and $X^4$ may be nitrogen.

Y may be an aliphatic group having 1-12 carbon atoms. In a preferred embodiment, Y may be an aliphatic group having 1-4 carbon atoms.

In a second aspect, the invention provides a method of synthesizing a compound of said first aspect, comprising at least one step selected from the group consisting of:

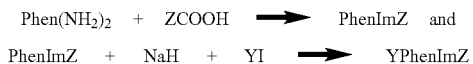

wherein Y is selected from the group consisting of hydrogen, substituted or unsubstituted aryl group, and substituted or unsubstituted aliphatic group having 1-24 carbon atoms which may be straight, branched or cyclic; Z is selected from the group consisting of phenyl, biphenyl, naphthyl, anthryl, phenanthryl, pyrenyl, pyridyl, bipyridyl, indyl, and quinolinyl; and wherein a said substituent is selected from the group consisting of an aryl group, an alkoxy group, a hydroxy group, a halo group, an amino group, a nitro group, a nitrile group, —$CF_3$ and an aliphatic group having 1-24 carbon atoms which may be straight, branched or cyclic.

In a third aspect, the invention provides a method of synthesizing a compound of said first aspect comprising at least one step selected from the group consisting of:

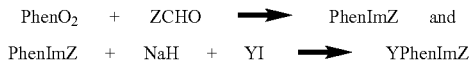

wherein Y is selected from the group consisting of hydrogen, substituted or unsubstituted aryl group, and substituted or unsubstituted aliphatic group having 1-24 carbon atoms which may be straight, branched or cyclic; Z is selected from the group consisting of phenyl, biphenyl, naphthyl, anthryl, phenanthryl, and pyrenyl; and wherein a said substituent is selected from the group consisting of an aryl group, an alkoxy group, a hydroxy group, a halo group, an amino group, a nitro group, a nitrile group, —$CF_3$ and an aliphatic group having 1-24 carbon atoms which may be straight, branched or cyclic.

In other aspects, the invention provides a photoluminescent or electroluminescent compound having a formula selected from the group consisting of PhenImAn (2), MePhenImAn (3), PhenImPy (4), and MePhenImPy (5).

In another aspect, the invention provides a composition comprising a compound of general formula (1), an organic polymer and a solvent. In a further aspect, the invention provides a composition comprising a photoluminescent or electroluminescent compound of general formula (1), an organic polymer and a solvent.

In another aspect, the invention provides a photoluminescent product or an electroluminescent product comprising a compound of general formula (1). The product may be a flat panel display device. It may be a luminescent probe.

In yet another aspect, the invention provides a method of producing electroluminescence, comprising the steps of: providing an electroluminescent compound of general formula (1) and applying a voltage across said compound so that said compound electroluminesces.

In a further aspect the invention provides an electroluminescent device for use with an applied voltage, comprising: a first electrode, an emitter which is an electroluminescent compound of general formula (1), and a second, transparent electrode, wherein voltage is applied to the two electrodes to produce an electric field across the emitter so that the emitter electroluminesces.

In a still further aspect, the invention provides an electroluminescent device for use with an applied voltage, comprising: a first electrode, a second, transparent electrode, an electron transport layer adjacent the first electrode, a hole transport layer adjacent the second electrode, and an emitter which is an electroluminescent compound of general formula (1) interposed between the electron transport layer and the hole transport layer, wherein voltage is applied to the two electrodes to produce an electric field across the emitter so that the emitter electroluminesces.

In another aspect, the invention provides a method of detecting metal ions comprising the steps of: providing a photoluminescent compound of general formula (1), and detecting photoluminescence of said compound, wherein contact with a metal ion quenches said photoluminescence of said compound. The metal ions may be selected from the group consisting of $Zn^{2+}$, $Cu^{2+}$, $Ni^{2+}$, $Cd^{2+}$, $Hg^{2+}$ and $Ag^+$.

In yet another aspect, the invention provides a method of detecting acid comprising the steps of: providing a photoluminescent compound of general formula (1), and detecting photoluminescence of said compound, wherein protonation of said compound changes the state of said compound's photoluminescence.

In another aspect, the invention provides a method of harvesting photons comprising the steps of: providing a compound of general formula (1), and providing light such that photons strike said compound and charge separation occurs in said compound. The separated charges may recombine and photons be released. Alternatively, the separated charges may migrate to respective electrodes to produce a potential difference and current flow.

In another aspect, the invention provides a method of separating charges comprising the steps of: providing a compound of general formula (1) and providing light such that photons strike said compound and charge separation occurs in said compound. The separated charges may recombine and photons be released. Alternatively, the separated charges may migrate to respective electrodes to produce a potential difference and current flow.

In respective further aspects, the invention provides a photocopier, a photovoltaic device, a photoreceptor, a solar cell and a semiconductor employing the afore-mentioned method of harvesting photons or the afore-mentioned method of separating charges.

In a still further aspect, the invention provides a molecular switch comprising a compound of general formula (1) that is capable of existing in more than one luminescent state, wherein acid, base, and/or incident light produces a change in the luminescent state of said compound. In certain embodiments, said compound may be 2-(9-anthryl)imidazo[4,5-f]-[1,10]phenanthroline (2) or 2-(2-pyridyl)imidazo[4,5-f]-[1,10]phenanthroline (4).

In another aspect, the invention provides a circuit comprising a said molecular switch.

BRIEF DESCRIPTION OF THE DRAWINGS

For a better understanding of the present invention and to show more clearly how it may be carried into effect, reference will now be made by way of example to the accompanying drawings, which illustrate aspects and features according to preferred embodiments of the present invention, and in which.

DETAILED DESCRIPTION OF THE INVENTION

Figure 1:
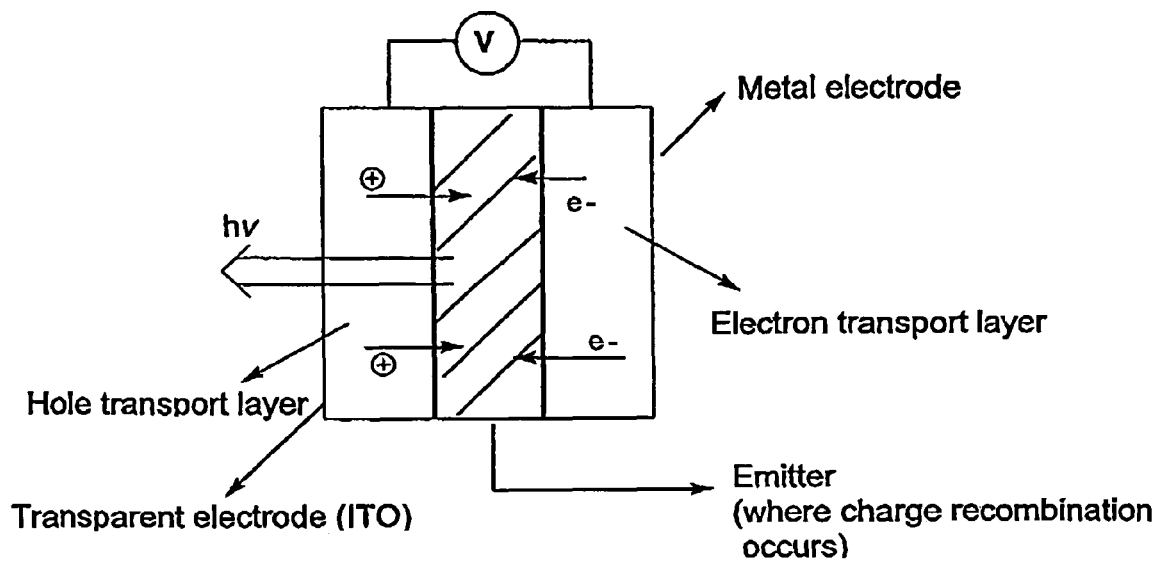
FIG. 1 shows a preferred embodiment of a three layer electroluminescent (EL) display device according to the invention.

In a first aspect of the invention, a stable organic compound of the general formula (1) is provided:

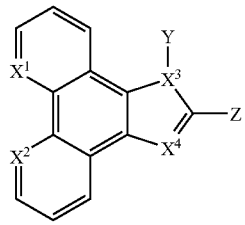

(1)

where $X^1$, $X^2$, $X^3$ and $X^4$ are each independently selected from the group consisting of carbon and nitrogen;

Y is selected from the group consisting of hydrogen, substituted or unsubstituted aryl group, and substituted or unsubstituted aliphatic group having 1-24 carbon atoms which may be straight, branched or cyclic;

Z is a substituted or unsubstituted aryl moiety selected from the group consisting of phenyl, biphenyl, naphthyl, anthryl, phenanthryl, pyrenyl, pyridyl, bipyridyl, indyl, and quinolinyl (preferred substituent examples 1a-1m are pictured below); and wherein a said substituent is selected from the group consisting of an aryl group, an alkoxy group, a hydroxy group, a halo group, an amino group, a nitro group, a nitrile group, —$CF_3$ and an aliphatic group having 1-24 carbon atoms which may be straight, branched or cyclic. As used herein "aliphatic" includes alkyl, alkenyl and alkynyl. An aliphatic group may be substituted or unsubstituted. It may be straight chain, branched chain or cyclic.

As used herein "aryl" includes heteroaryl and may be substituted or unsubstituted.

As used herein "unsubstituted" refers to any open valence of an atom being occupied by hydrogen.

As used herein "substituted" refers to the structure having one or more substituents.

Preferably a compound of formula (1) exhibits intense luminescence, which may be photoluminescence and/or electroluminescence. Preferably, Y is 1-4 carbon atoms.

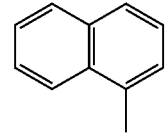

1-naphthyl

1a

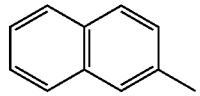

2-naphthyl

1b

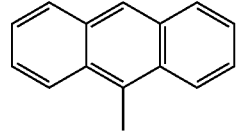

9-anthryl

1c

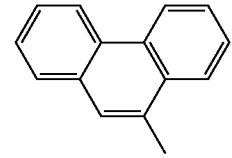

9-phenanthryl

1d

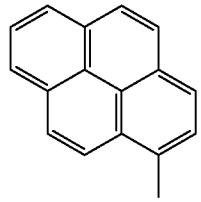

1-pyrenyl

1e

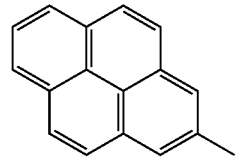

2-pyrenyl

1f

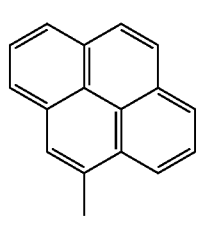

4-pyrenyl

1g

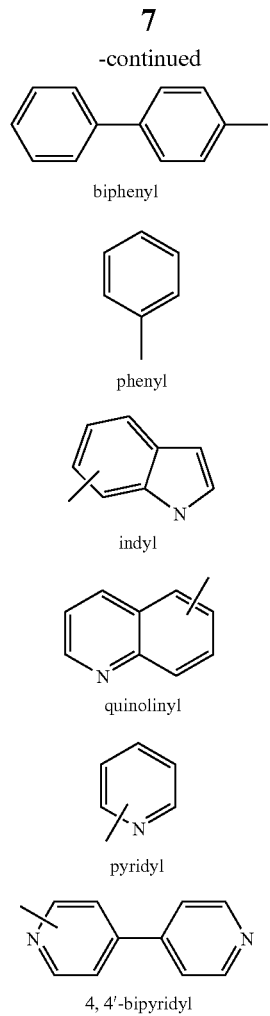

biphenyl phenyl indyl quinolinyl pyridyl 4,4'-bipyridyl

In preferred embodiments, $X^1$, $X^2$, $X^3$ and $X^4$ are each independently a substituted or unsubstituted carbon (an unsubstituted carbon has hydrogen as its substituent(s)) or an unsubstituted nitrogen. In some embodiments, one, two or three of $X^1$, $X^2$, $X^3$ and $X^4$ are nitrogen. In a preferred embodiment, $X^1$, $X^2$, $X^3$ and $X^4$ are all nitrogen. A synthetic scheme depicting the preparation of such compounds is pictured in Schemes 1 and 2; working examples of detailed synthetic procedures are provided in Examples 1-4.

Scheme 1. Preparation of precursors for Scheme 2.

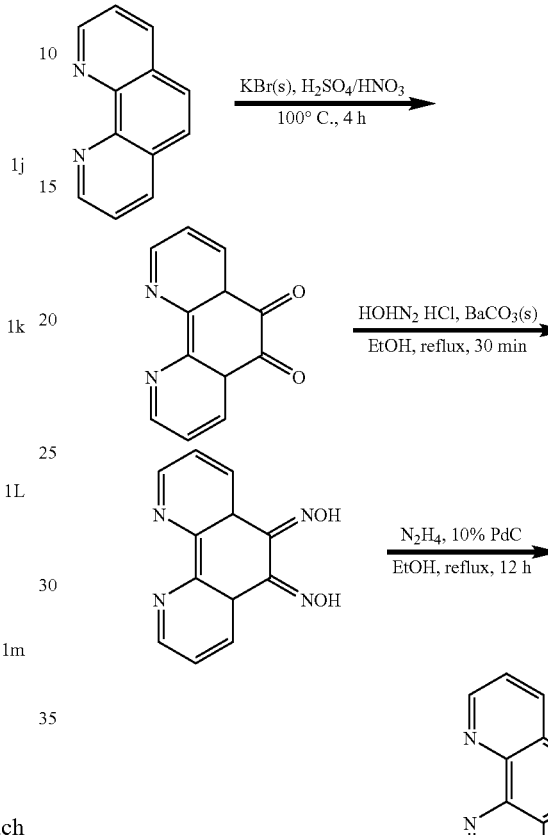

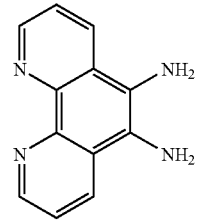

Scheme 2. Preparation of compounds of the general formula (1).

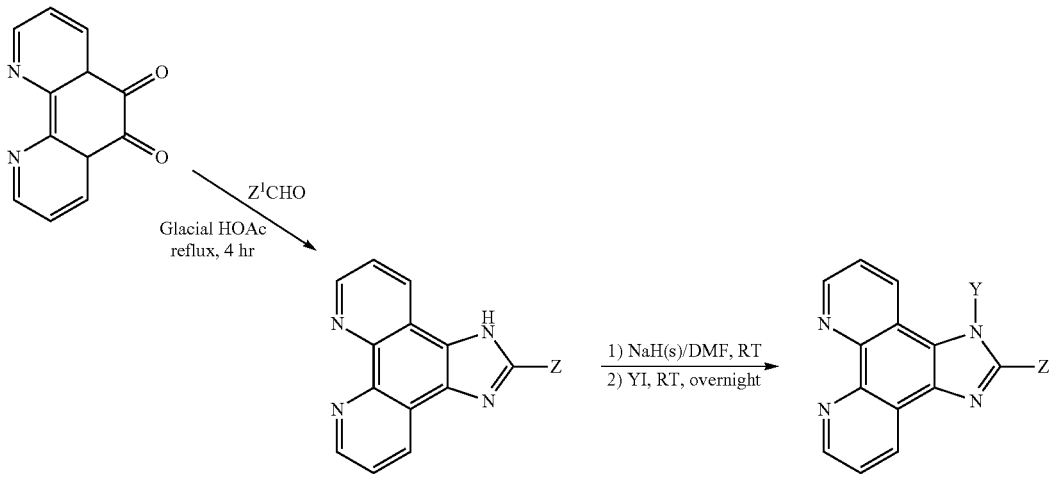

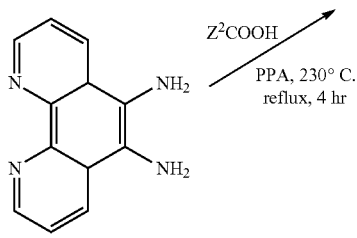

wherein Y is selected from the group consisting of hydrogen, substituted or unsubstituted aryl group, and substituted or unsubstituted aliphatic group having 1-24 carbon atoms which may be straight, branched or cyclic;

$Z^1$ is selected from the group consisting of substituted or unsubstituted phenyl, biphenyl, naphthyl, anthryl, phenanthryl, and pyrenyl;

$Z^2$ is selected from the group consisting of $Z^1$, substituted or unsubstituted pyridyl, bipyridyl, indyl, and quinolinyl; and wherein a said substituent is selected from the group consisting of an aryl group, an alkoxy group, a hydroxy group, a halo group, an amino group, a nitro group, a nitrile group, —$CF_3$ and an aliphatic group having 1-24 carbon atoms which may be straight, branched or cyclic.

In some embodiments, Y is an aliphatic group having 1-12 carbons. In some embodiments, Y is an aliphatic group having 1-4 carbons.

In yet another embodiment, this aspect of the invention provides compounds wherein $X^1$, $X^2$, $X^3$ and $X^4$ are each carbon. Preparation of precursors that are analogous to those in Scheme 1 but in which $X^1$, $X^2$, $X^3$ and $X^4$ are each carbon is described in Yamazaki, 2001. Such precursors can then be reacted according to Scheme 2.

Thus, the invention provides, for example, compounds PhenImAn (2), MePhenImAn (3), PhenImPy (4), MePhenImPy (5), which have the following structures:

PhenImAn:
2-(9-anthryl)imidazo[4,5-f]-1,10]phenanthroline (2)

(2)

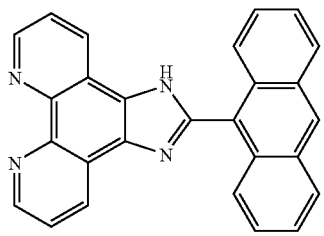

MePhenImAn: 1-methyl-2-(9-anthryl)imidazo[4,5-f]-1,10]phenanthroline (3)

(3)

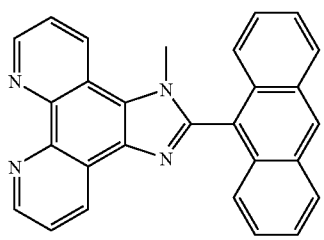

PhenImPy:
2-(2-pyridyl)imidazo[4,5-f]-[1,10]-phenanthroline
(4)

(4)

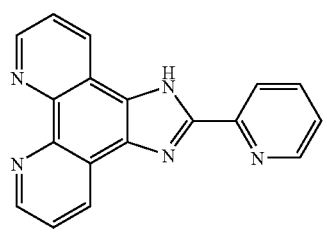

MePhenImPy: 1-methyl-2-(2-pyridyl)imidazo[4,5-f]-[1,10]-phenanthroline (5)

(5)

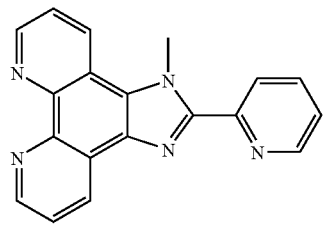

The invention provides compounds that are photoluminescent and, in at least some embodiments of the invention, electroluminescent; they can produce intense light.

The invention also provides a method of producing photoluminescence comprising the steps of: providing a photoluminescent compound of the invention having a formula as set out above; and irradiating said photoluminescent compound with radiation of a wavelength suitable for exciting the compound to photoluminescence.

The invention further provides a method of producing electroluminescence comprising the steps of: providing an electroluminescent compound of the invention having a formula as set out above; and applying a voltage across said electroluminescent compound.

The invention further provides an electroluminescent device for use with an applied voltage, comprising: a first electrode, an emitter (e.g., phosphor) which is an electroluminescent compound of the invention, and a second, transparent electrode, wherein a voltage is applied between the two electrodes to produce an electric field across the emitter. The emitter consequently electroluminesces. In some embodiments of the invention, the device includes one or more charge transport layers interposed between the emitter and one or both of the electrodes. For example, spacing of a preferred embodiment of the device, called for the purposes of the present specification a "three layer EL device", is: first electrode, first charge transport layer, emitter, second charge transport layer, and second, transparent electrode.

A particularly preferred compound according to this aspect of the invention, which has been shown to exhibit blue photoluminescence and blue electroluminescence, is MePhenImAn (3), for which a preferred synthetic protocol is described in Example 2. Example 5, referring to FIGS. 10-12, describes photoluminescence and electroluminescence work on this compound employing a device made and operated at Xerox Research Centre of Canada (Mississauga, Ontario).

An advantage of preferred compounds of the invention is that they are highly soluble in common organic solvents such as toluene, diethyl ether, tetrahydrofuran (THF), and dichloromethane. This permits the compounds to be blended easily and conveniently with organic polymers. The role of the organic polymer in such a mixture is at least two-fold: First, a polymer can provide protection for the compound from air degradation. Second, a polymer host matrix permits the use of a spin-coating or dip-coating process as an alternative way to make films. Although spin-coating and dip-coating processes may not produce as high quality films as those produced by chemical vapor deposition or vacuum deposition, they are often much faster and more economical.

Accordingly, the invention further provides methods of applying compounds as described above to a surface. These methods include solvent cast from solution, electrochemical deposition, vacuum vapor deposition, chemical vapor deposition, spin coating and dip coating. The compounds may be applied alone or with a carrier. In some embodiments of the invention, they are applied in a composition including an organic polymer. Such compositions are also encompassed by the invention.

As an example of this application, the MePhenImPy (5) compound forms a clear transparent solution with the weakly-luminescent polymer poly(N-vinylcarbazole) (PVK) in $CH_2Cl_2/C_6H_5Cl$. This can be converted to a transparent film by evaporating the toluene solvent via either a dip-coating or spin-coating process. Films obtained in this way are stable. Certain polymers such as, for example, PVK, are expected to further enhance the luminescence of an emitter in the film. Conveniently, spin coating may be performed using a Chemat Technology spin-coater KW-4A; and vacuum deposition may be performed using a modified Edwards manual diffusion pump.

The invention provides a method of producing electroluminescence comprising the steps of: providing an electroluminescent compound of the invention having the general formula (1) as set out above; and applying a voltage across said electroluminescent compound so that the compound electroluminesces.

According to the invention, electroluminescent devices for use with an applied voltage are provided. In general, such a device has a first electrode, an emitter which is an electroluminescent compound of the invention, and a second, transparent electrode, wherein a voltage is applied between the two electrodes to produce an electric field across the emitter of sufficient strength to cause the emitter to electroluminesce. Preferably, the first electrode is of a metal, such as, for example, aluminum, which reflects light emitted by the compound; whereas the second, transparent electrode permits passage of emitted light therethrough. The transparent electrode is preferably of indium tin oxide (ITO) glass or an equivalent known in the art. Here, the first electrode is the cathode and the second electrode is the anode.

Referring to FIG. 1, a preferred embodiment of an electroluminescent device of the invention is shown. The emitter is interposed between an electron transport layer (e.g., tris-(8-hydroxyquinoline)aluminum ($Alq_3$) or 2-(biphenyl-4-yl)-5-(4-tert-butyl phenyl)-1,3,4-oxadiazole (PBD)) adjacent the first metal electrode and a hole transport layer (e.g., N,N'-di-1-naphthyl-N,N'-diphenylbenzidiine (NPB)) adjacent the second, transparent electrode. The choice of the materials employed as charge transport layers will depend upon the specific properties of the particular emitter employed. The hole transport layer or the electron transport layer may also function as a supporting layer. The device is connected to a voltage source such that an electric field of sufficient strength is applied across the emitter. Light, preferably blue light, consequently emitted from the compound of the invention passes through the transparent electrode.

In some embodiments of the invention, the device includes one or more charge transport layers interposed between the emitter and one or both of the electrodes. Such charge transport layer(s) are employed in prior art systems with inorganic salt emitters to reduce the voltage drop across the emitter. In a first example of such a device, layers are arranged in a sandwich in the following order: first electrode, charge transport layer, emitter, second charge transport layer, and second transparent electrode. In a preferred embodiment of this type, a substrate of glass, quartz or the like is employed. A reflective metal layer (corresponding to the first electrode) is deposited on one side of the substrate, and an insulating charge transport layer is deposited on the other side. The emitter layer which is a compound of the invention is deposited on the charge transport layer, preferably by vacuum vapor deposition, though other methods may be equally effective. A transparent conducting electrode (e.g., ITO) is then deposited on the emitter layer. An effective voltage is applied to produce electroluminescence of the emitter.

In a second example of an EL device of the invention, a second charge transport layer is employed, and the sandwich layers are arranged in the following order: first electrode, first charge transport layer, emitter, second charge transport layer and second, transparent electrode.

Electroluminescent devices of the invention may include one or more of the blue-emitting compounds described herein. In some embodiments of the invention, an electroluminescent device such as a flat panel display device may include not only a blue-emitting phosphor as described herein, but may be a multiple-color display device including one or more other phosphors. The other phosphors may emit in other light ranges, e.g., red, green, and/or be "stacked" relative to each other. Convenient materials, structures and uses of electroluminescent display devices are described in Rack et al., 1996.

For photoluminescence, the compounds absorb energy from ultraviolet radiation and emit visible light near the ultraviolet end of the visible spectrum e.g., in the blue region. For electroluminescence, the absorbed energy is from an applied electric field. The luminescence of, for example, PhenImAn (2) and MePhenImAn (3) can be readily quenched by the addition of acid or metal cations such as $Zn^{2+}$, $Cu^{2+}$, $Ni^{2+}$, $Cd^{2+}$, $Hg^{2+}$, $Ag^+$ and $H^+$. For example, when $Zn(AcO)_2$ is added to a dimethylformamide (DMF) solution of MePhenImAn (3), the bright blue luminescence of the solution changes gradually to very weak yellow:

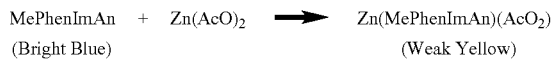

MePhenImAn + Zn(AcO)$_2$ → Zn(MePhenImAn)(AcO$_2$)
(Bright Blue)                    (Weak Yellow)

Figure 6:
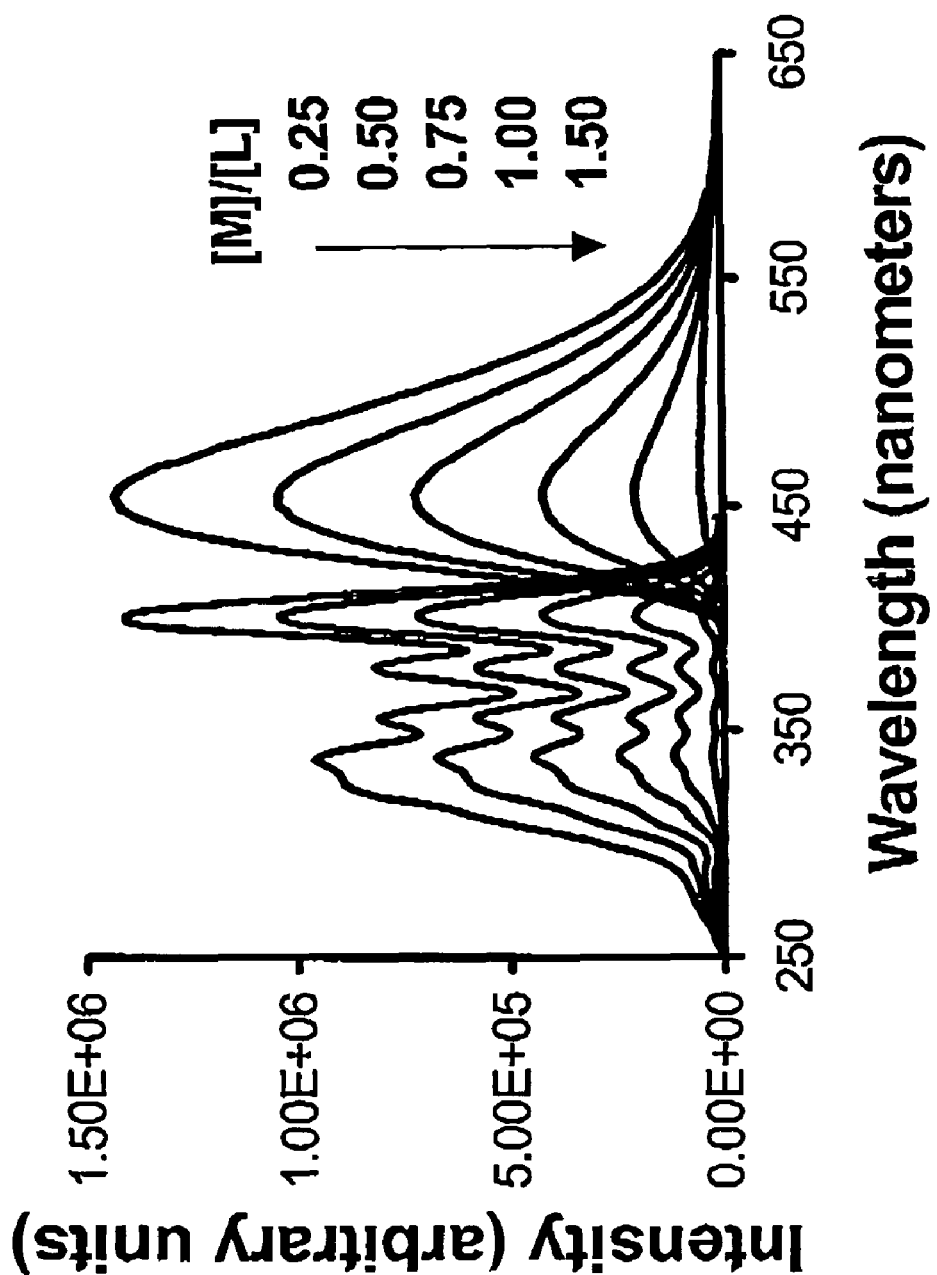
FIG. 6 shows the change of the luminescence spectra of MePhenImAn (3) in DMF, at a concentration of $1.0\times10^{-5}$ M with the addition of $Zn(OAc)_2$ at a concentration of $1.0\times10^{-3}$ M at 298K.
Figure 7:
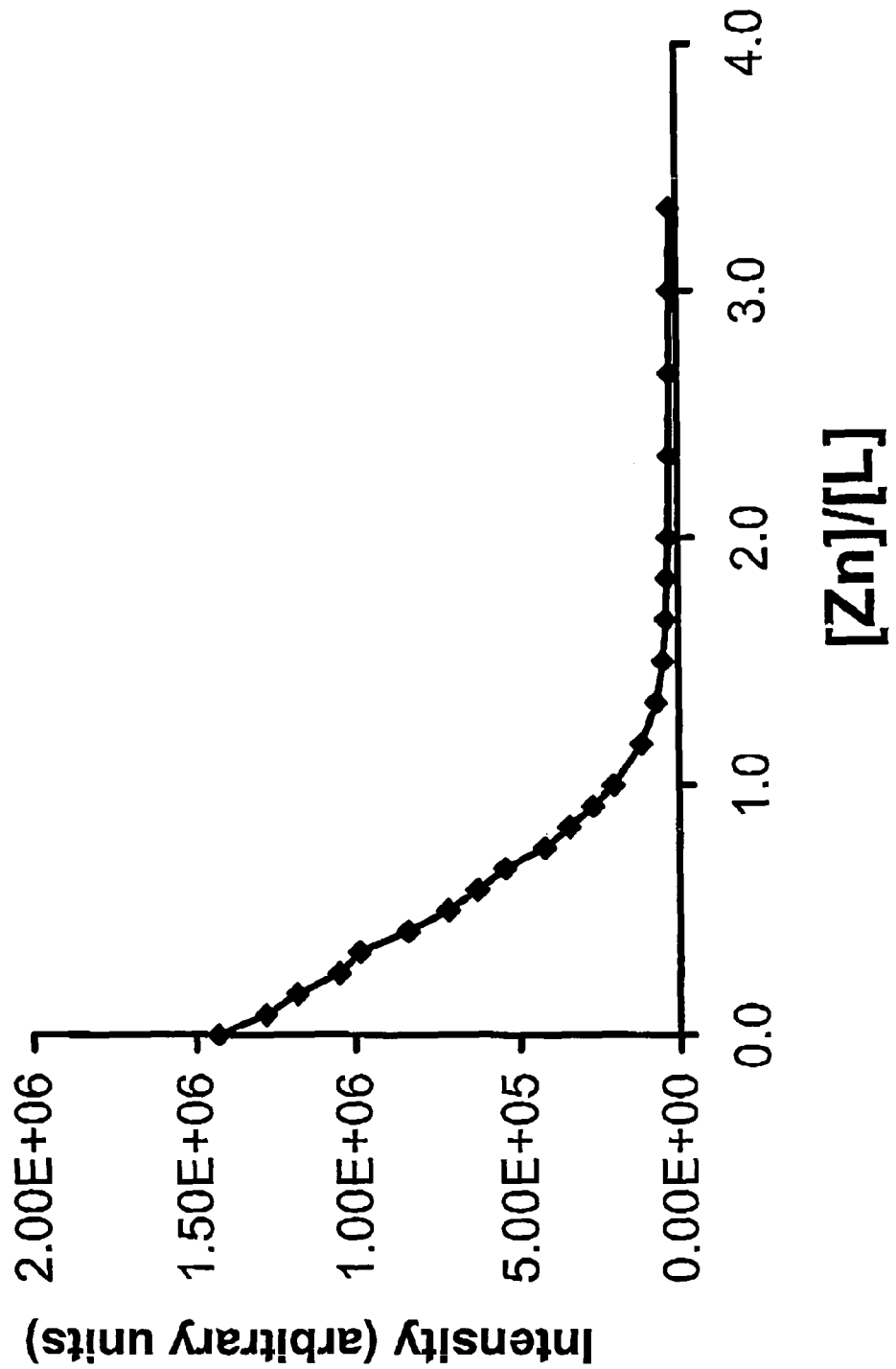
FIG. 7 shows the change of emission intensity of MePhenImAn (3) in DMF at a concentration of $1.0\times10^{-5}$ M at 478 nanometers with the addition of $Zn(OAc)_2$ in DMF at a concentration of $1.0\times10^{-3}$ M at 298K.
Figure 15:
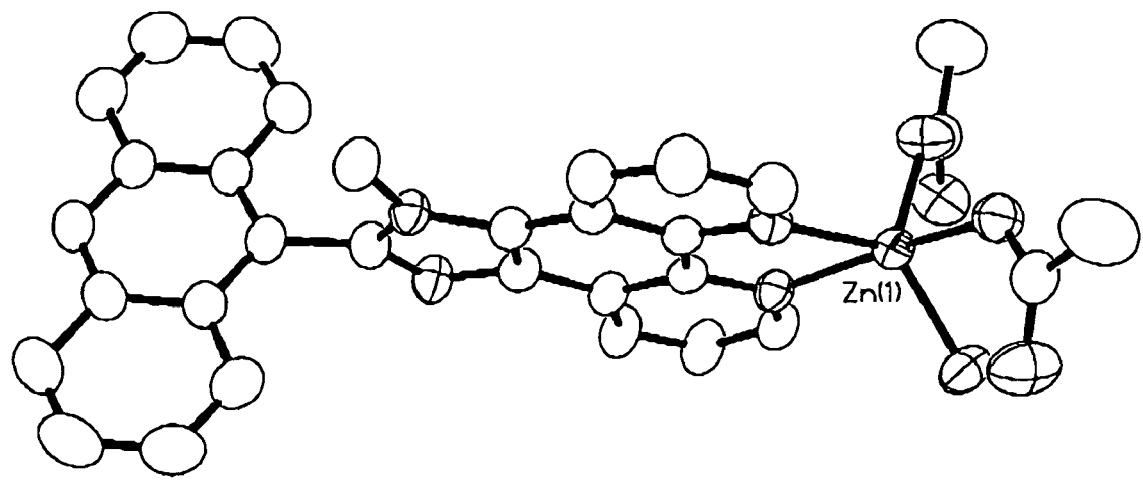
FIG. 15 shows the crystal structure of $[Zn(MePhenImAn)(AcO)_2(H_2O)]$.

The quenching process is shown in FIG. 6 and FIG. 7, which indicate the formation of a 1:1 metal:ligand (L) complex, as confirmed by x-ray single crystal structure analysis shown in FIG. 15.

The invention further provides methods employing compounds of the invention to harvest photons, and corresponding devices for such use. Spectroscopic studies have demonstrated that compounds of the invention have high efficiency to harvest photons and produce highly polarized electronic transitions. In general, when such compounds are excited by light, a charge separation occurs within the molecule; a first portion of the molecule has a negative charge and a second portion has a positive charge. Thus the first portion acts as an electron donor and the second portion as an electron acceptor. If recombination of the charge separation occurs, a photon is produced and luminescence is observed. In photovoltaic devices, recombination of the charge separation does not occur; instead the charges move toward an anode and a cathode to produce a potential difference, from which current can be produced.

Molecules with the ability to separate charges upon light initiation are useful for applications such as photocopiers, photovoltaic devices and photoreceptors. Organic photoconductors provided by the present invention are expected to be useful in such applications, due to their stability and ability to be spread into thin films. Related methods are encompassed by the invention.

Organic semiconducting materials can be used in the manufacture of photovoltaic cells that harvest light by photoinduced charge separation. To realize an efficient photovoltaic device, a large interfacial area at which effective dissociation of excitons occurs must be created; thus an electron donor material is mixed with an electron acceptor material. (Here, an exciton is a mobile combination of an electron and a hole in an excited crystal, e.g., a semiconductor.) Organic luminescent compounds as semiconductors are advantageous due to their long lifetime, efficiency, low operating voltage and low cost.

Photocopiers use a light-initiated charge separation to attract positively-charged molecules of toner powder onto a drum that is negatively charged.

Figure 14:
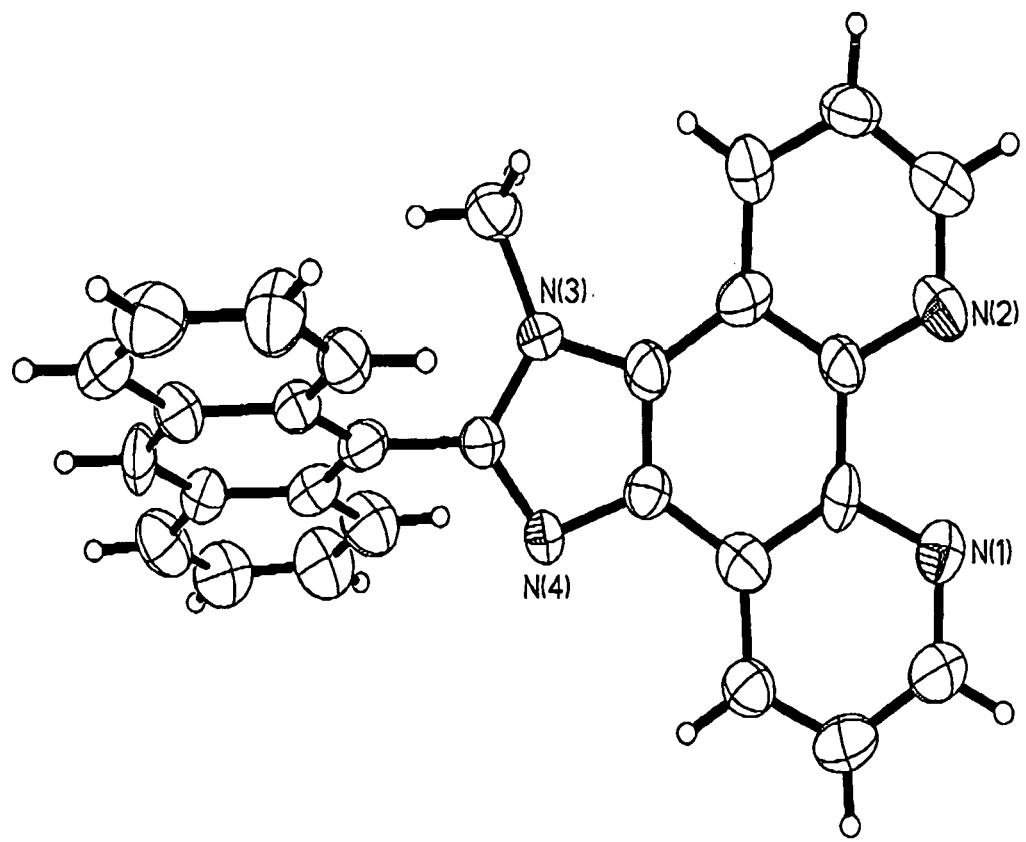
FIG. 14 shows the crystal structure of MePhenImAn (3)

The invention further provides methods employing compounds of the invention to detect metal ions. As an example, FIG. 14 shows the change in emission intensity of MePhenImAn (3) with the addition of Zn$^{2+}$. The change in the luminescence upon coordination of metal ions may be useful for detection of gunpowder residue, bomb making activity, and/or environmental contamination such as heavy metal contamination of food or soil or water, as well as for detection of sites of meteor impact and even interplanetary exploration.

Figure 8:
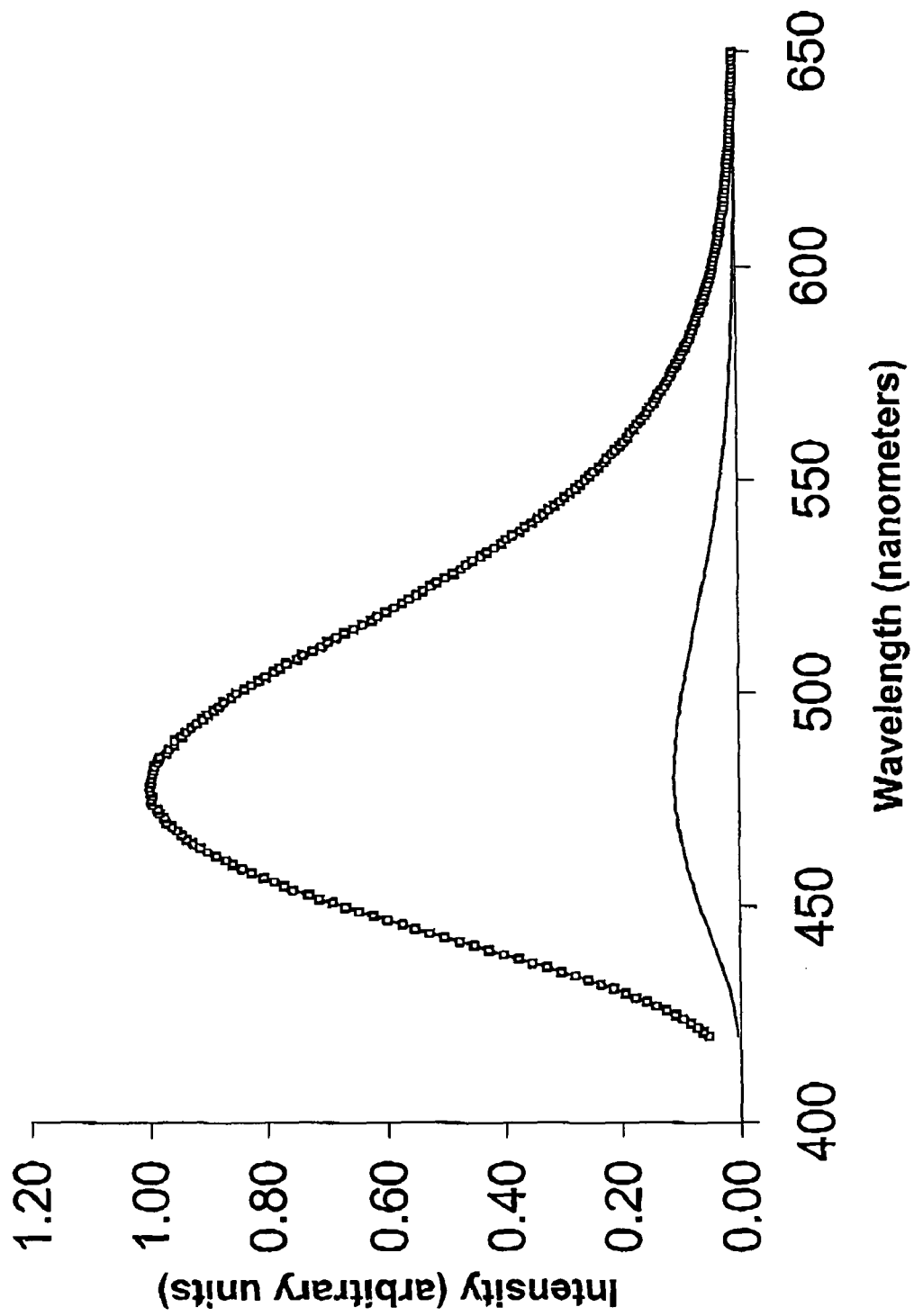
FIG. 8 shows the change of emission intensity of PhenImAn (2) in DMF at a concentration of $2.5\times10^{-4}$ M with the addition of 0 equivalents (□□□), and 5 equivalents (—) of $H^+$ added as aqueous HCl at 298K.
Figure 9:
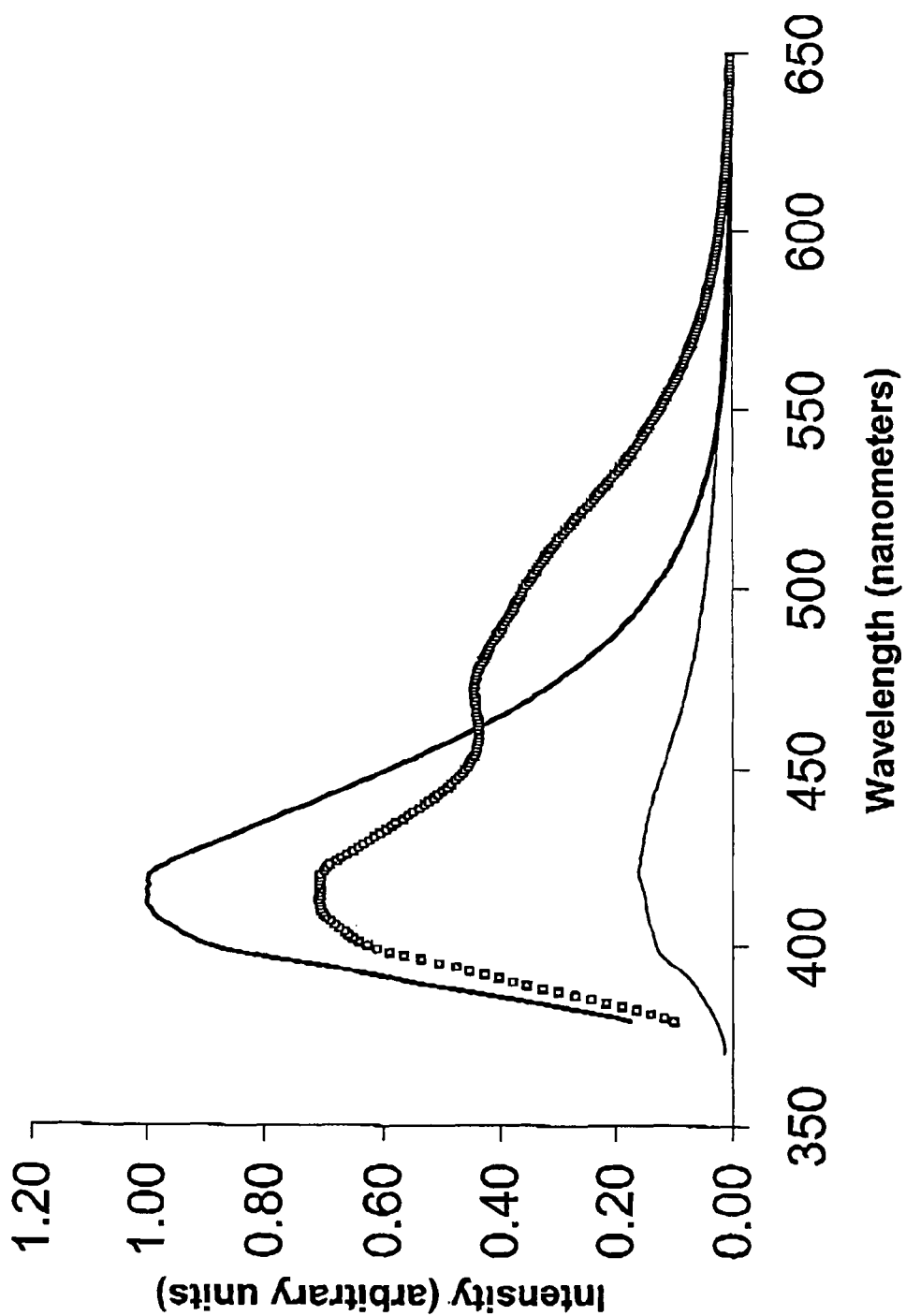
FIG. 9 shows the change of emission intensity of PhenImPy (4) in DMF, $\lambda_{max}$=369 nm at a concentration of $2.5\times10^{-4}$ M with the addition of 0 equivalents (—), 0.20 equivalents (□□□) and 5 equivalents (—) of $H^+$ added as aqueous HCl at 298K.

The invention further provides methods employing compounds of the invention to detect acid. As an example, FIG. 8 and FIG. 9 show the change in the emission intensity of PhenImAn (2) and PhenImPy(4), respectively, with the addition of 5 equivalents of acid. This aspect of the invention is expected to be useful for a variety of applications, including, without limitation, pH sensors, as well as detection of contamination, particularly environmental contamination (e.g., acidity of lakes, soil, etc.).

The invention further provides molecular switches employing compounds as described above, and methods of use thereof. In a preferred embodiment, the compounds PhenImAn (2) and PhenImPy (4) are employed. These compounds can exist in three different states (protonated, neutral and deprotonated).

Information processing systems of current computers are based on semiconductor logic gates or switches (Tang et al., 1987). By reducing the switching elements to a molecular level, the processing capability and memory density of computers could be increased by several orders of magnitude and the power input could be decreased significantly (Leung et al., 2000). Candidates for this purpose are molecules that are capable of undergoing reversible transformations in response to chemical, electrical and/or optical stimulation, and producing readily detectable optical signals in the process. For example, the respective neutral forms of PhenImAn (2) and PhenImPy (4), when in solution, emit blue luminescence. The neutral forms can be easily converted to the non-luminescent protonated forms by the addition of acid. These can be switched back to the deprotonated forms by the addition of a base. Three-state molecular circuits based on PhenImAn (2) and PhenImPy (4) with OH$^-$, H$^+$ and ultraviolet light as inputs and visible light as outputs have been established.

Examples 1 to 4 below provide detailed descriptions of the syntheses of compounds (2), (3), (4), and (5), respectively. As would be apparent to a person of ordinary skill in the art, other functionalities may be included in derivatives according to the invention. Alternatively, starting materials may be modified to include, but are not limited to, functionalities such as ether, epoxide, ester, amide or the like. Such functionalities may in some cases confer desirable physical or chemical properties, such as increased stability or luminescence.

WORKING EXAMPLES

All starting materials were purchased from Aldrich Chemical Company and used without further purification. Solvents were freshly distilled over appropriate drying reagents. All experiments were carried out under a dry nitrogen atmosphere using standard Schlenk Techniques unless otherwise stated. Thin Layer Chromatography was carried out on SiO$_2$ (silica gel F254, Whatman). Flash chromatography was carried out on silica (silica gel 60, 70-230 mesh). $^1$H and $^{13}$C spectra were recorded on a Bruker Avance 300 spectrometer operating at 300 and 75.3 MHz respectively. Excitation and emission spectra were recorded on a Photon Technologies International QuantaMaster Model 2 spectrometer. Data collection for the X-ray crystal structural determinations were performed on a Bruker SMART CCD 1000 X-ray diffractometer with graphite-monochromated Mo K$_\alpha$ radiation ($\lambda$=0.71073 Å) at 298K and the data were processed on a Pentium PC using the Bruker AXS Windows NT SHELXTL software package (version 5.10). Elemental analyses were performed by Canadian Microanalytical Service Ltd., (Delta, B.C., Canada). Melting points were determined on a Fisher-Johns melting point apparatus.

Though not specifically described in the working examples set forth below, conveniently EL spectra may be obtained using Ocean Optics HR2000; and data involving current, voltage and luminosity may be obtained using a Keithley 238 high current source measure unit.

Example 1

Figure 2:
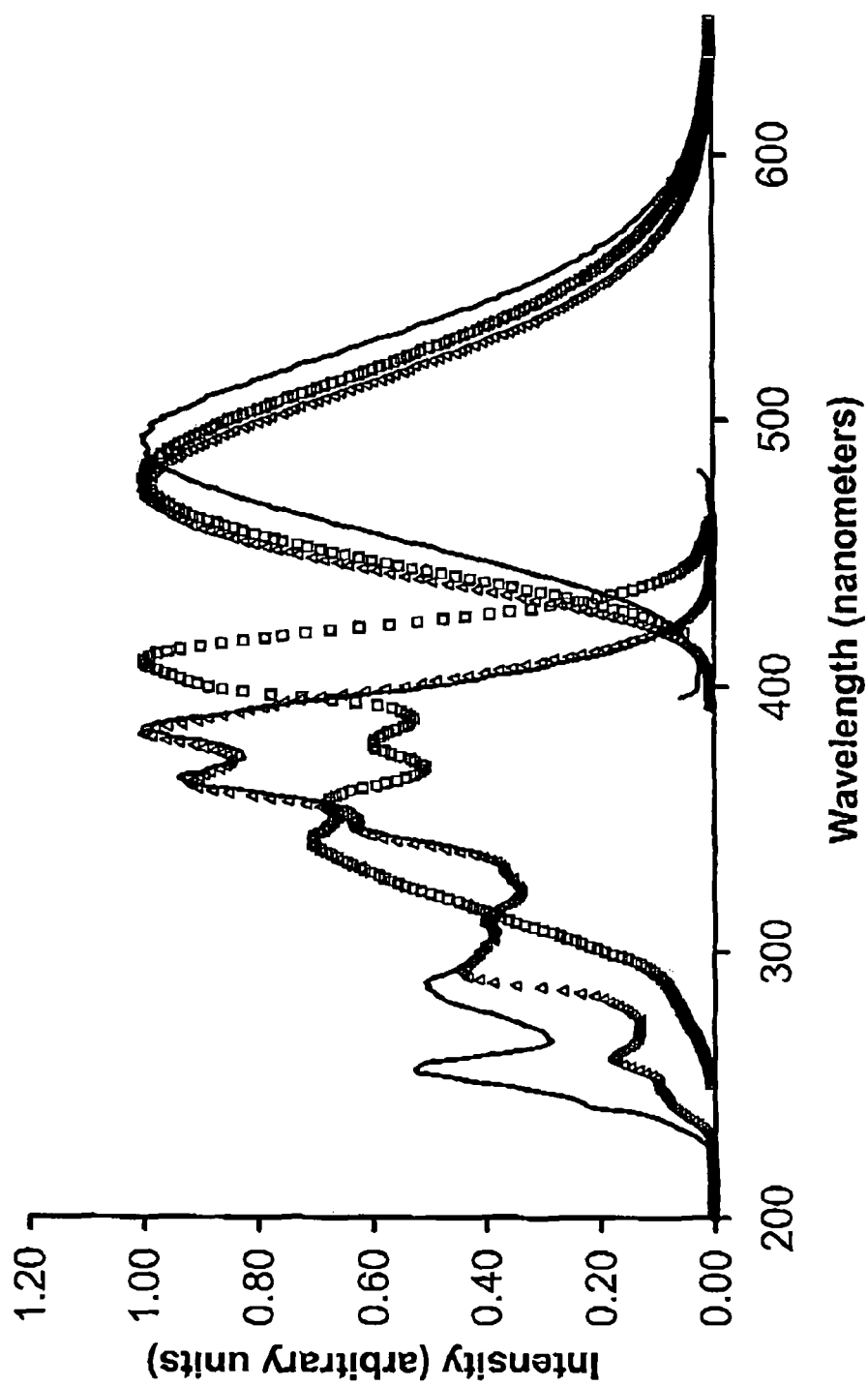
FIG. 2 shows the luminescence spectra of PhenImAn (2) in DMF (□□□), THF (ΔΔΔ) and methylene chloride (—) at a concentration of $1.0 \times 10^{-5}$ M.
Figure 13:
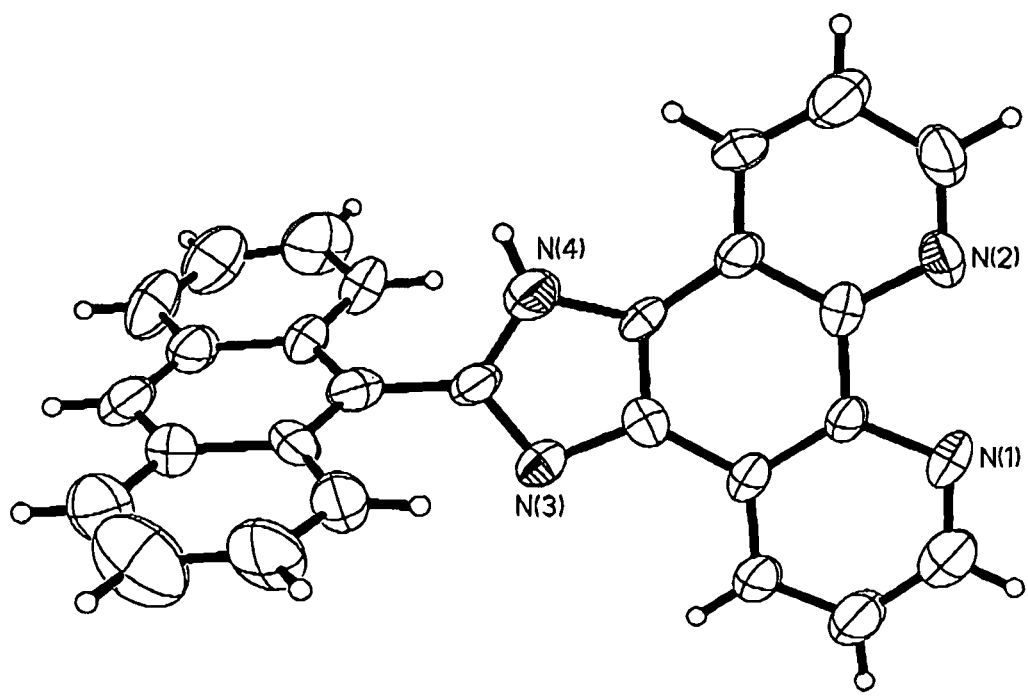
FIG. 13 shows the crystal structure of PhenImAn (2)

Synthesis of PhenImAn (2). 3.0 mmol of Phendione, 60 mmol of NH$_4$Ac(s) and 3.3 mmol of 9-anthrylaldehyde were added to 100 mL glacial acetic acid and the mixture was refluxed for 4 hours under $N_2(g)$. The mixture was then cooled to room temperature and 500 mL of water was added with stirring. A dark yellow solid was obtained immediately. The solid was then collected by filtration and washed thoroughly with water and then acetone. The product PhenImAn (2) was dried in vacuo and was obtained at 82% yield. $^1$H Nuclear Magnetic Resonance (NMR) (500 MegaHertz (MHz), $d_4$-methanol, −50° C., referenced to tetramethylsilane (TMS)): chemical shift (δ) in parts per million (ppm)=9.17 (d, $^3J$=4.0 Hz, 2H, phen), 9.07 (dd, $^3J$=8.0 Hz, $^4J$=2.0 Hz, 1H, phen), 8.92 (s, 1H, anthryl), 8.78 (dd, $^3J$=8.0 Hz, $^4J$=2.0 Hz, 1H, phen), 8.29 (d, $^3J$=8.5 Hz, 2H, anthryl), 7.96 (m, 2H, phen), 7.85 (d, $^3J$=9.0 Hz, 2H, anthryl), 7.65 (dd, $^3J_1$=$^3J_2$=7.0 Hz, 2H, anthryl), 7.60 (dd, $^3J_1$=$^3J_2$=8.5 Hz, 2H, anthryl). Elemental analysis calculated (%) for $C_{27}H_{16}N_4 \cdot 1/3H_2O$: C, 80.56; H, 4.19; N, 13.92. Found: C, 80.63; H, 4.12; N, 13.93. The compound was characterized by X-ray single crystal analysis, its molecular structure is shown in FIG. 13. The luminescent spectra in different solvents are shown in FIG. 2, in DMF, $\lambda_{max}$=268 nm, Molar Absorptivity Coefficient (ε)=4.7×10$^5$ M$^{-1}$ cm$^{-1}$; in tetrahydrofuran, $\lambda_{max}$=256 nm, ε=1.2×10$^5$ M$^{-1}$ cm$^{-1}$; in methylene chloride, $\lambda_{max}$=256 nm, 5.4×10$^5$ M$^{-1}$ cm$^{-1}$.

Example 2

Figure 3:
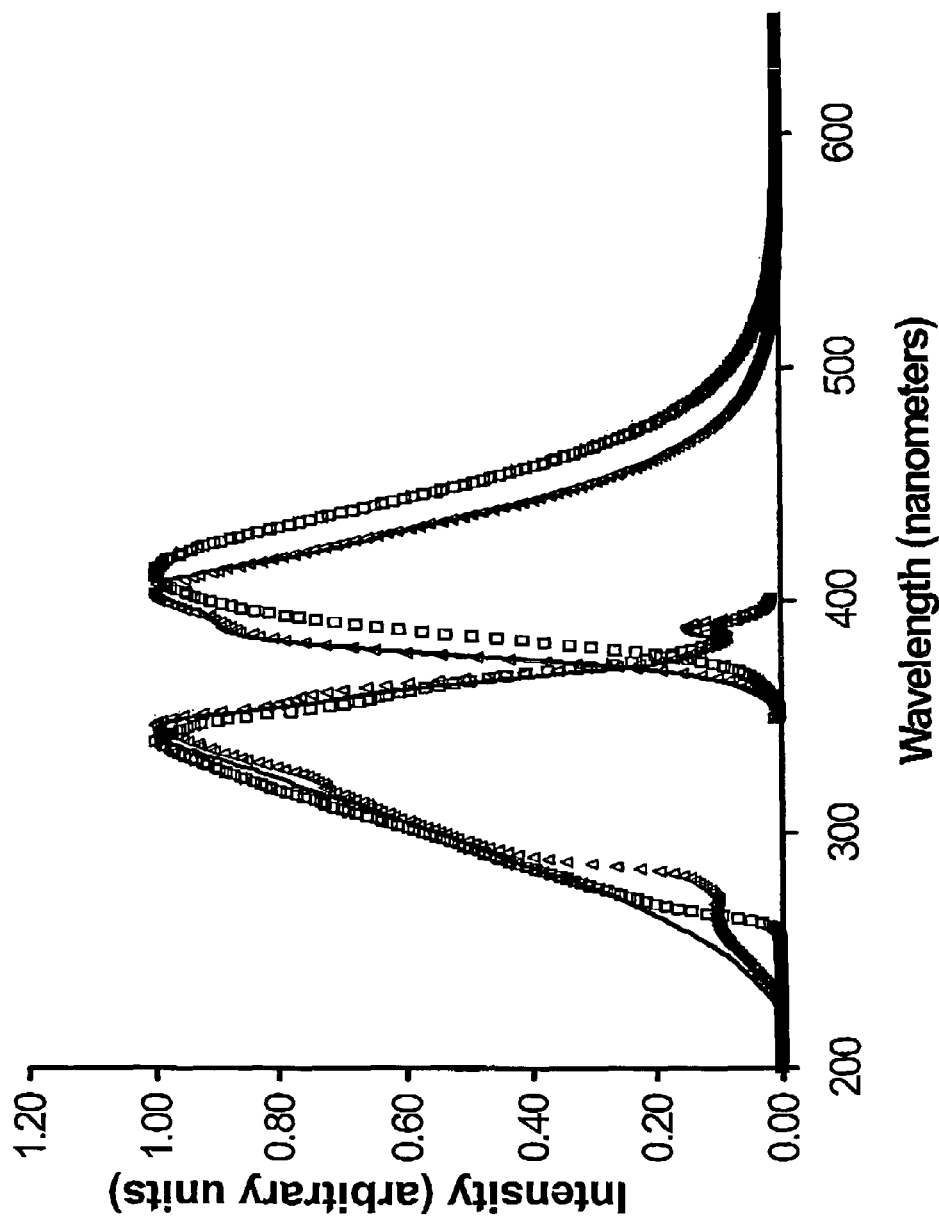
FIG. 3 shows the luminescence spectra of MePhenImAn (3) in DMF (□□□), THF (ΔΔΔ) and methylene chloride (—) at a concentration of $1.0 \times 10^{-5}$ M.

Synthesis of MePhenImAn (3). 3.5 mmol of NaH (s) (60% dispersion in mineral oil) was suspended in 20 mL dry DMF under $N_2(g)$. 0.7 mmol of PhenImAn (2) (s) was then added to the suspension in portions with stirring. The mixture was stirred for 20 minutes and 3.5 mmol of $CH_3I$ in 10 mL dry DMF was added dropwisely. The mixture was stirred at ambient temperature overnight and was then filtered. The filtrate was poured into 100 mL water and extracted with methylenechloride (25 mL×4). The organic layers were combined and washed with water (25 mL×2) and dried over $K_2CO_3$(s). The solvent was removed under vacuum and product MePhenImAn (3) was obtained as a light yellow solid, at 86% yield. $^1$H NMR (400 MHz, in $d_2$-ethylenechloride, 25° C.): δ=9.18 (dd, $^3J$=9.6 Hz, $^4J$=2.0 Hz, 1H, phen), 9.17 (dd, $^3J$=9.6 Hz, $^4J$=1.6 Hz, 1H, phen), 9.08 (dd, $^3J$=8.0 Hz, $^4J$=1.6 Hz, 1H, phen), 8.88 (dd, $^3J$=8.4 Hz, $^4J$=1.6 Hz, 1H, phen), 8.78 (s, 1H, anthryl), 8.20 (d, $^3J$=8.4 Hz, 2H, phen), 7.76 (m, 2H, anthryl), 7.59 (m, 4H, anthryl), 7.49 (m, 2H, anthryl), 3.26 (s, 3H, methyl). The compound was characterized by X-ray single crystal analysis. The molecular structure is shown in FIG. 14. The luminescent spectra in different solvents are shown in FIG. 3.

Example 3

Figure 4:
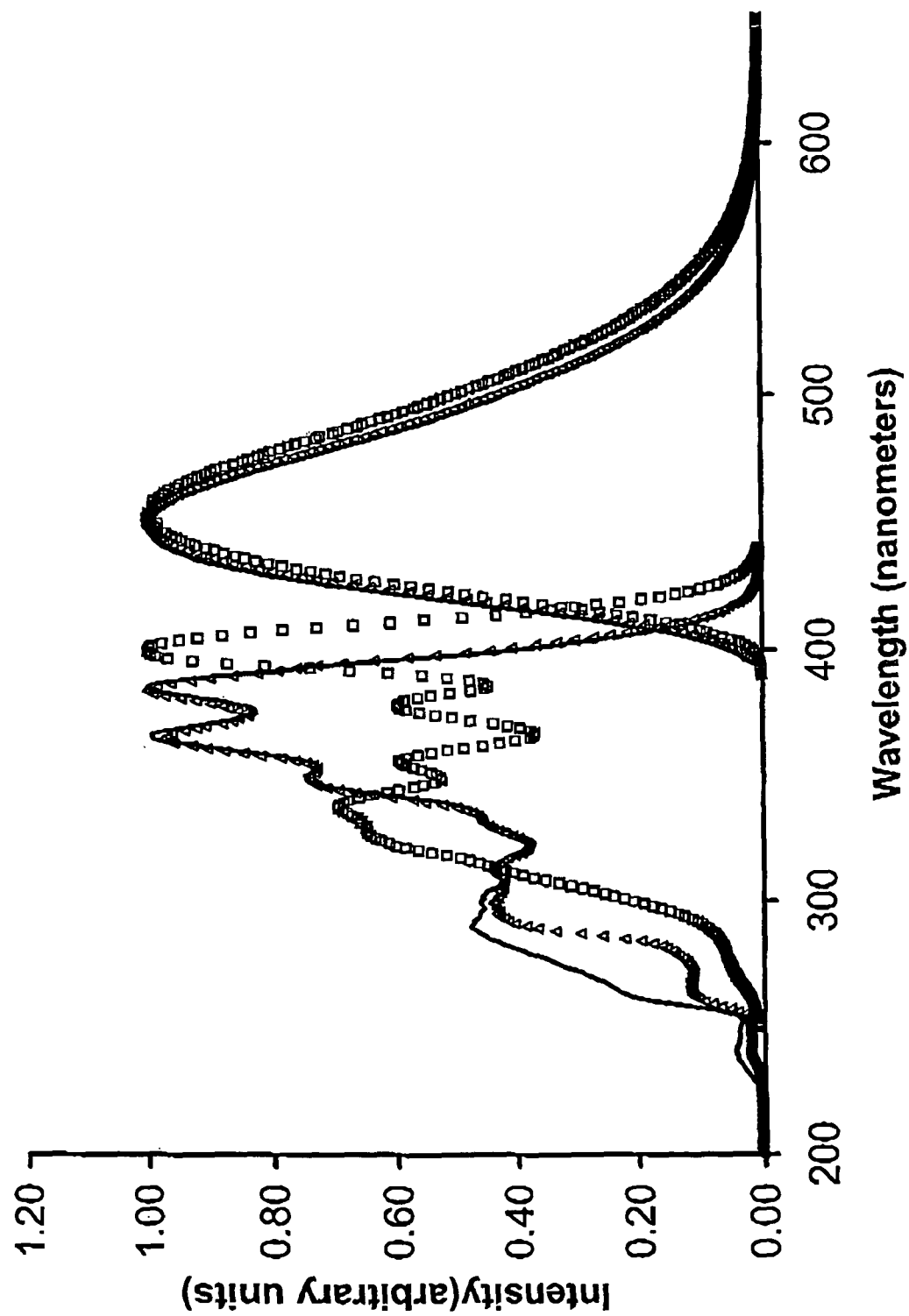
FIG. 4 shows the luminescence spectra of PhenImPy (4) in DMF (□□□), THF (ΔΔΔ) and methylene chloride (—) at a concentration of $1.0 \times 10^{-5}$ M.

Synthesis of PhenImPy (4). 2.2 mmol of 5,6-diamino-1,10-phenathroline and 2.5 mmol of picolinic acid were dissolved in 8 mL polyphosphoric acid (PPA). The mixture was then heated to 230° C. under $N_2(g)$ and was kept at this temperature for 4 hours. The resulting black sticky liquid was poured into 20 mL of vigorously stirred cold water. A dark brown solid appeared immediately. The solid was collected by filtration and then slurried in 50 mL hot 10% $Na_2CO_3$ solution. The resulting solid was washed well with water and acetone, and dried under vacuum. PhenImPy (4) was obtained as a light brown solid, at 85% yield. $^1$H NMR (300 MHz, $d_4$-methanol, 25° C., TMS): δ ppm=9.08 (dd, $^3J$=8.1 Hz, $^4J$=1.5 Hz, 2H, phen), 8.90 (dd, $^3J$=4.5 Hz, $^4J$=1.8 Hz, 2H, phen), 8.67 (d, $^3J$=6.0 Hz, 1H, py), 8.36 (d, $^3J$=9.0 Hz, 1H, py), 7.92 (ddd, $^3J_1$=$^3J_2$=6.0 Hz, $^4J$=3.0 Hz, 1H, py), 7.72 (dd, $^3J_1$=8.1 Hz, $^3J_2$=4.2 Hz, 2H, phen), 7.34 (m, 1H, py). Elemental analysis calculated (%) for $C_{18}H_{11}N_5$: C, 72.72; H, 3.73; N, 23.56. Found: C, 72.60; H, 3.75; N, 23.62%. The luminescent spectra in different solvents are shown in FIG. 4, in DMF, $\lambda_{max}$=274 nm, Molar Absorptivity Coefficient (ε)=3.1×10$^4$ M$^{-1}$ cm$^{-1}$; in tetrahydrofuran, $\lambda_{max}$=276 nm, ε=4.2×10$^4$ M$^{-1}$ cm$^{-1}$; in methylenechloride, $\lambda_{max}$=278 nm, 4.6×10$^5$ M$^{-1}$ cm$^{-1}$.

Example 4

Figure 5:
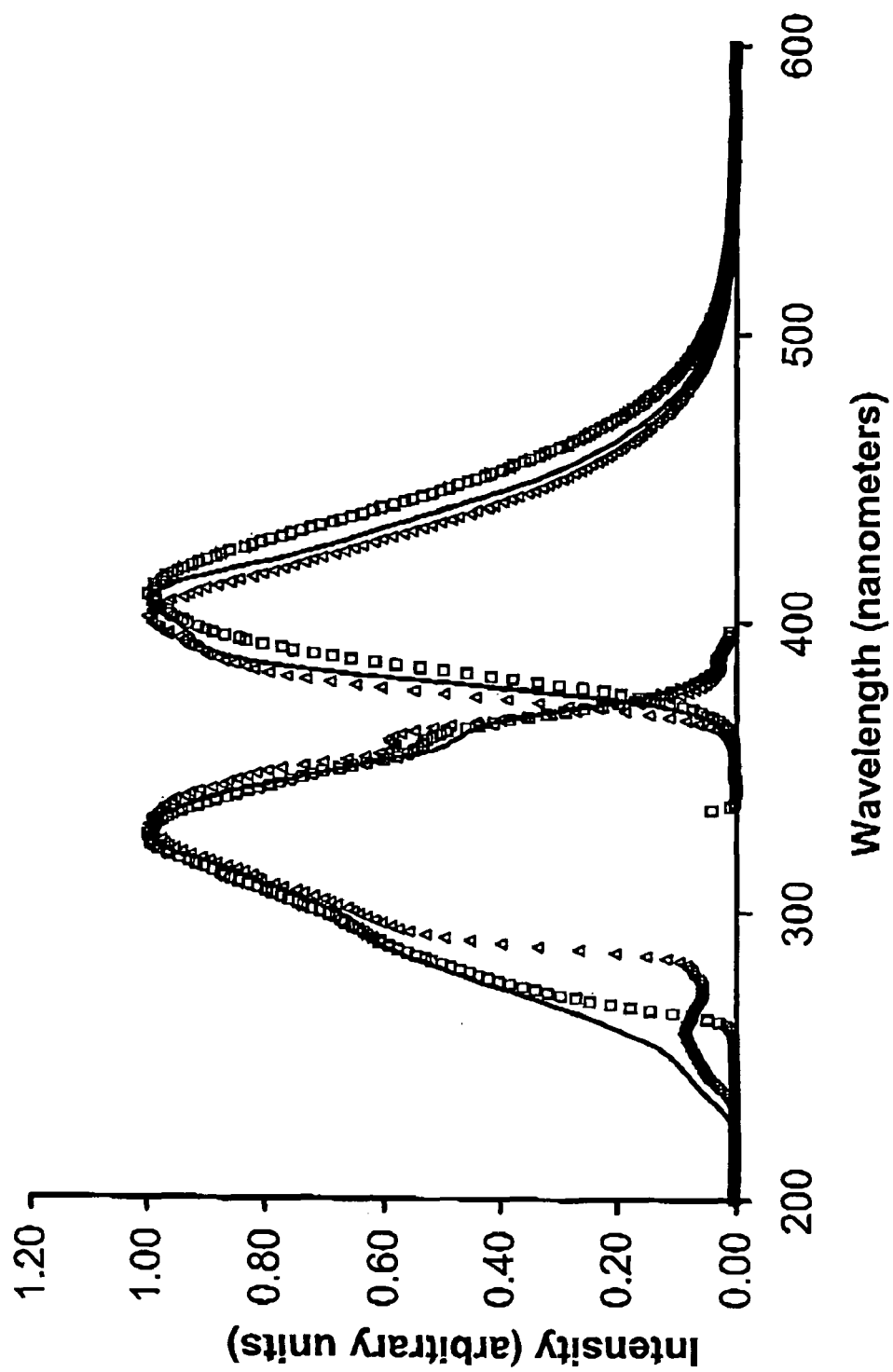
FIG. 5 shows the luminescence spectra of MePhenImPy (5) in DMF (□□□), THF (ΔΔΔ) and methylene chloride (—) at a concentration of $1.0\times10^{-5}$ M.

Synthesis of MePhenImPy (5). MePhenImPy (5) was synthesized by following the same procedure as MePhenImAn (3) using PhenImPy (4) in place of PhenImAn(2), with yield 83%. $^1$H NMR (300 MHz, d-chloroform, 25° C., TMS): δ ppm=9.21 (m, 2H, phen), 9.10 (dd, $^3J$=8.1 Hz, $^4J$=1.8 Hz, 1H, phen), 8.91 (d, $^3J$=8.4 Hz, $^4J$=1.5 Hz, 1H, phen), 8.78 (ddd, $^3J_1$=4.8 Hz, $^4J_2$=1.8 Hz, $^5J$=0.9 Hz, 1H, py), 8.46 (ddd, $^3J$=7.2 Hz, $^4J$=$^5J$=1.2 Hz, 1H, py), 7.95 (ddd, $^3J_1$=$^3J_2$=7.8 Hz, $^4J$=1.8 Hz, 1H, py), 7.75 (dd, $3J_1$=8.1 Hz, $^3J_2$=4.5 Hz, 1H, phen), 7.73 (dd, $^3J_1$=8.4 Hz, $^3J_2$=4.5 Hz, 1H, phen), 7.42 (ddd, $^3J_1$=7.5 Hz, $^3J_2$=4.8 Hz, $^4J$=1.2 Hz, 1H, py). Elemental analysis calculated (%) for $C_{19}H_{13}N_5$: C, 73.30; H, 4.20; N, 22.49. Found: C, 73.10; H, 4.25; N, 22.45%. The luminescent spectra in different solvents are shown in FIG. 5.

Example 5

Figure 10:
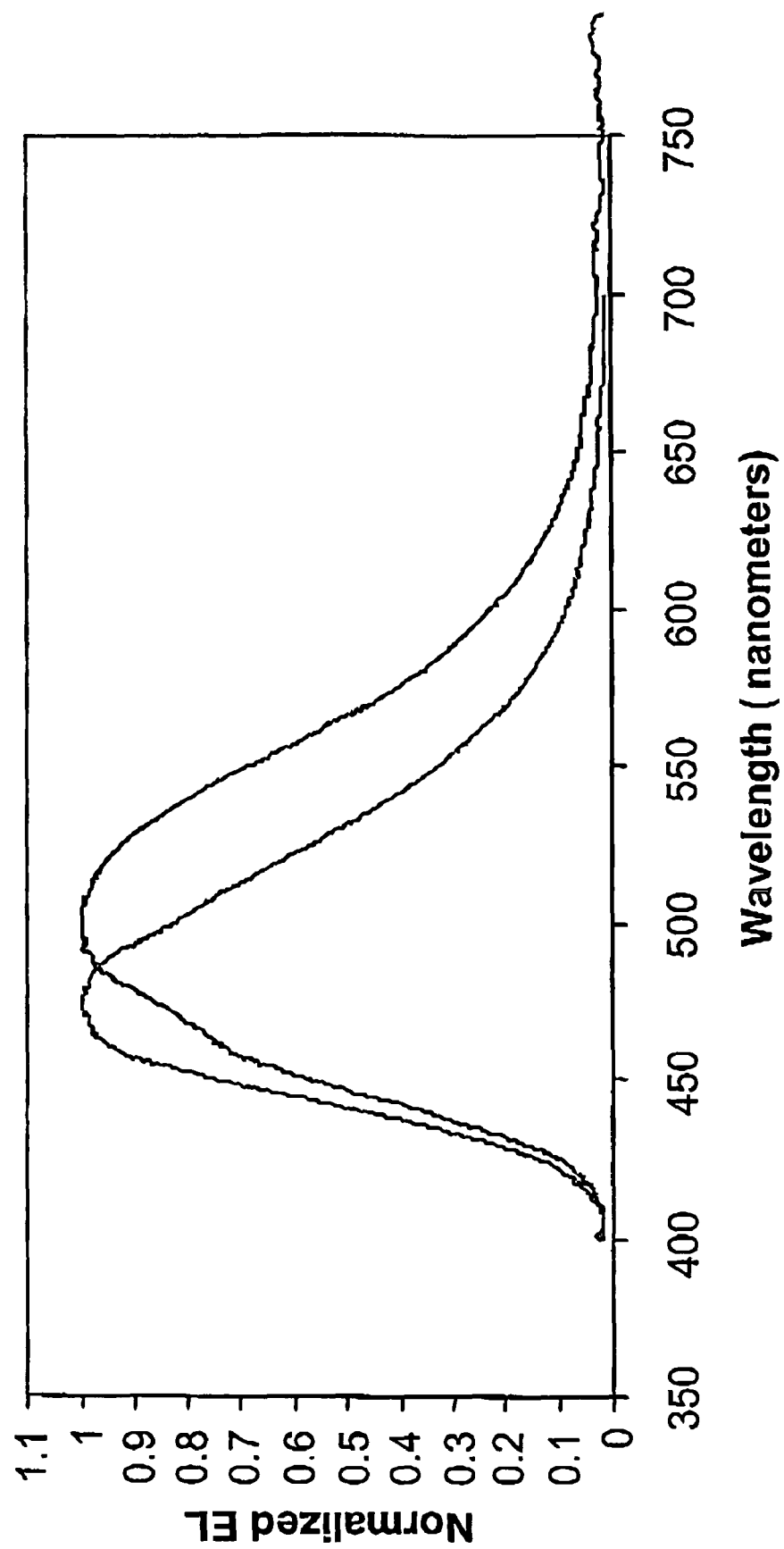
FIG. 10 shows photoluminescence ($\lambda_{max}$=475 nm) and electroluminescence ($\lambda_{max}$=505 nm) spectra for MePhenImAn (3) in a three layer device described in Example 5.
Figure 11:
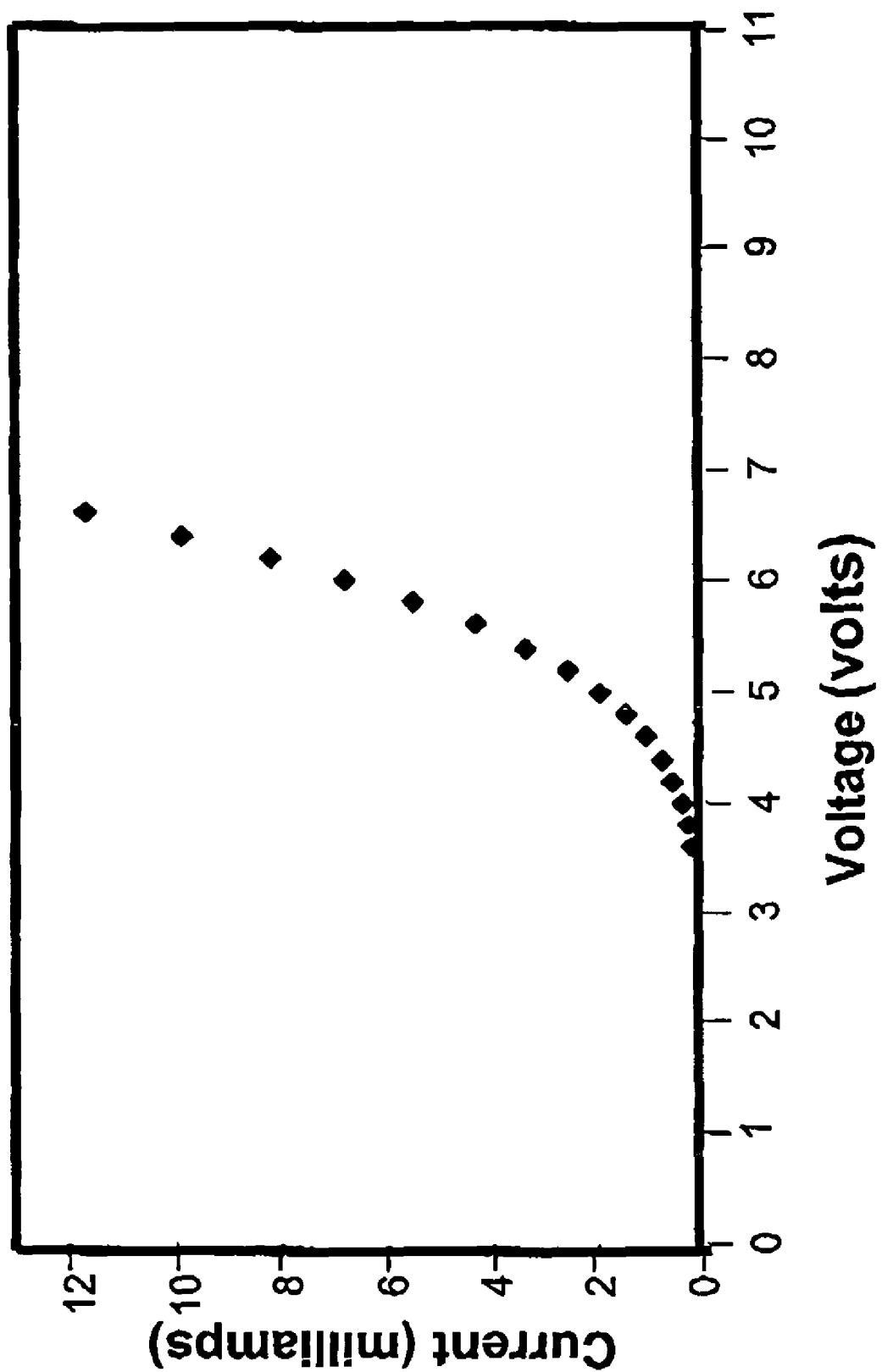
FIG. 11 shows a plot of current versus voltage that displays the electroluminescent efficiency obtained with MePhenImAn (3) in the device of FIG. 10.
Figure 12:
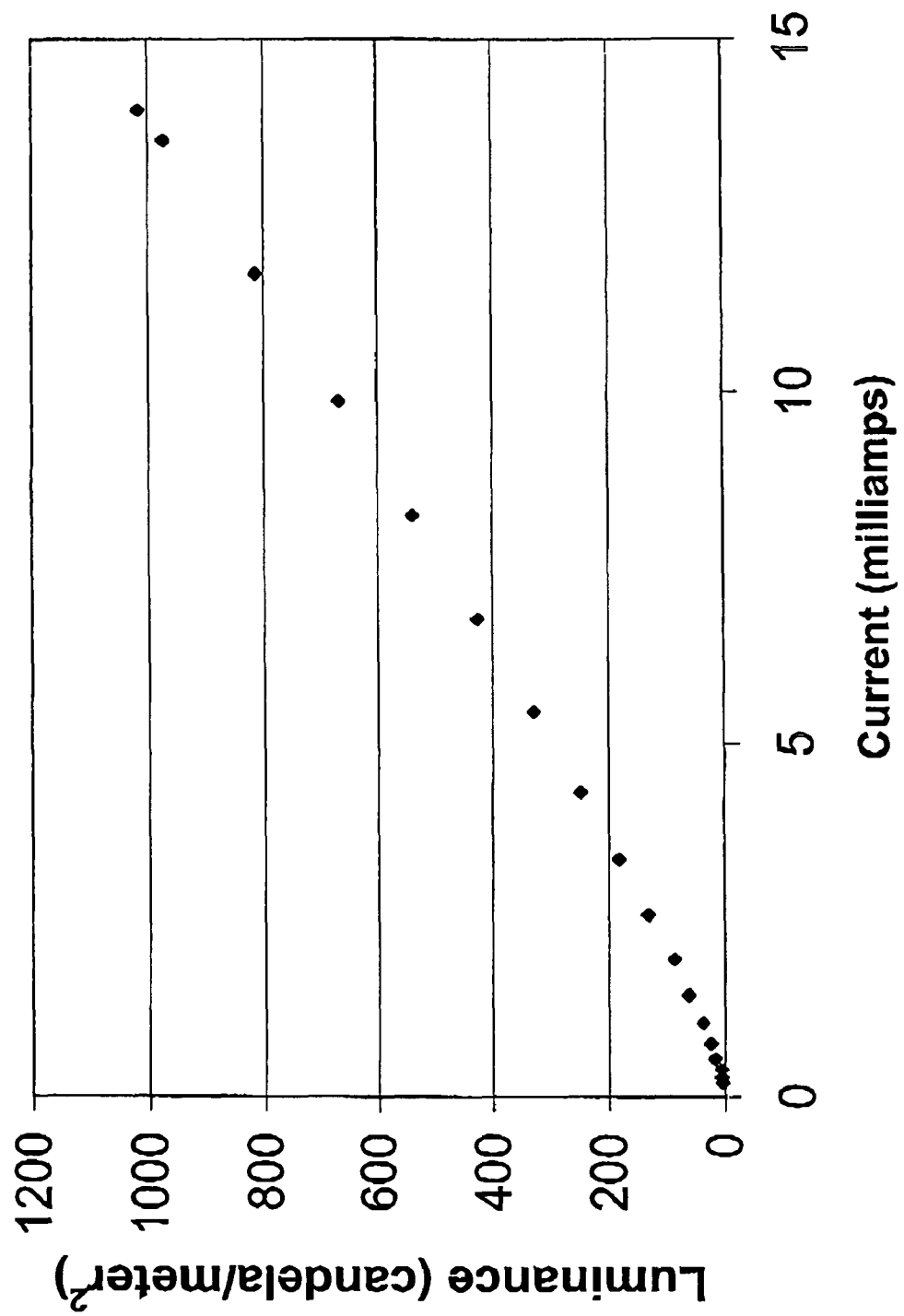
FIG. 12 shows a plot of luminance versus current that displays the brightness of the electroluminescence produced by device of FIGS. 10 and 11.

Preparation and operation of an EL device. FIG. 10 shows photoluminescence and electroluminescence spectra for MePhenImAn (3) obtained using a three layer EL device of the following configuration: cathode which is Mg:Ag (9:1); electron transport layer which is $Alq_3$ (thickness=200 nm); emitter which is MePhenImAn (thickness=300 nm); hole transport layer which is NPB (Van Slyke et al., 1996) (thickness=300 nm); and anode which is indium tin oxide (ITO). Device area was 8 square millimeters. FIG. 11 displays the voltage required to obtain a current from this device, and FIG. 12 shows the brightness of the electroluminescence obtained.

All scientific and patent publications cited herein are hereby incorporated in their entirety by reference.

Although this invention is described in detail with reference to preferred embodiments thereof, these embodiments are offered to illustrate but not to limit the invention. It is possible to make other embodiments that employ the principles of the invention and that fall within its spirit and scope as defined by the claims appended hereto.

REFERENCES

Ashenhurst, J.; Brancaleon, L; Hassan, A.; Liu, W.; Schmider, H.; and Wang, S. Blue Luminescent Organoaluminum Compounds: $Al_2(CH_3)_4$(7-azain)$_2$, $Al_2(CH_3)_2$(7-azain)$_4$, $Al_2(CH_3)(OCH(CF_3)_2)_3$(7-azain)$_2$, $Al_2(\mu\text{-}OCH(CF_3)_2(CH_3))$(7-azain)$_2$((OCH(CF_3)_2)_2$, $Al_3(\mu_3\text{-}O)(CH_3)$(7-azain)$_4$(OCH(CF_3)_2)_2$, and $Al_4(\mu_3\text{-}O)_2$(7-azain)$_6$(OCH(CF_3)_2)_2$ (7-azain=Deprotonated 7-Azaindole). *Organometallics* (1998) 17: 3186-3195.

Ashenhurst, J.; Brancaleon, L.; Gao, S.; Liu, W.; Schmider, H.; Wang, S.; Wu, G.; and Wu, Q. G. Blue Luminescent Organoaluminum Compounds: $Al(CH_3)_2$(dpa), $Al_2(CH_3)_5$(dpa)$_2$, $Al_4(O)_2(CH_3)_6$(dpa)$_2$, and $Al(pfap)_3$, dpa=Deprotonated Di-2-pyridylamine, pfap=Deprotonated 2-Pentafluoroanilinopyridine. *Organometallics* (1998) 17: 5334-5341.

Ashenhurst, J.; Wu, G.; and Wang, S. Syntheses, Structures, Solution, and Solid-State $^{27}$Al NMR Studies of Blue Luminescent Mononuclear Aluminum Complexes: Al(7-azain)₂(7-azain-H)(CH₃), Al(7-azain)₃(7-azain-H), and Al(7-azain)(7-azain-H)(OCH(CF₃)₂)₂ (7-azain-H=7-azaindole). *J. Am. Chem. Soc.* (2000)122: 2541-2547.

Gao, S.; Wu, Q.; Wu, G.; and Wang, S. Highly Fluxional Blue Luminescent Aluminum Complexes: Al(CH₃)(7-azain-2-Ph)₂(7-azainH-2-Ph), Al₃(m₃-O)(CH₃)₃(7-azain-2-Ph)₄, and Al₃((m₃-O)(CH₃)₃(7-azain-2-CH₃)₄, 7-azain=7-azaindole anion. *Organometallics* (1998)17: 4666-4674.

Hassan, A.; and Wang, S. First blue luminescent diborate compound: B2(m-O)Et₂(7-azain)₂ (7-azain=7-azaindole anion). *Chem. Commun.* (1998) 211-212.

Jia, W.-L.; Datong, S.; and Wang, S. Blue Luminescent Three-Coordinate Organoboron Compounds with 2,2'-Dipyridylamino Functional Group. *Journal of Organic Chemistry* (2003) 68: 701-705.

Koene, B.; Loy, D.; and Thompson, M. Unsymmetrical Triaryldiamines as Thermally Stable Hole Transporting Layers for Organic Light-Emitting Devices. *Chemistry of Materials*. (1998) 10(8): 2235-2250.

Leung, L. M.; Lo, W. Y.; So, S. K.; Lee, K. M.; and Choi, W. K. J A High-Efficiency Blue Emitter for Small Molecule-Based Organic Light-Emitting Diode. *J. Am. Chem. Soc.* (2000) 122: 5640-5641.

Liu, S.; Wu, Q.; Schmider, H. L.; Aziz, H.; Hu, N.; Popovic, Z.; and Wang, S. Syntheses, Structures, and Electroluminescence of New Blue/Green Luminescent Chelate Compounds: Zn(2-py-in)₂(THF), BPh₂(2-py-in), Be(2-py-in)₂, and BPh₂(2-py-aza), 2-py-in=2-(2-pyridyl)indole, 2-py-aza=2-(2-pyridyl)-7-azaindole. *J. Am. Chem. Soc.* (2000) 122: 3671-3678.

Pang, J.; Marcotte, E. J.-P.; Seward, C.; Brown, R. S.; and Wang, S. A blue luminescent star-shaped Zn¹¹ complex that can detect benzene. *Angew. Chem. Int. Ed.* (2001)40: 4021-4042.

Rack, P. D.; Naman, A.; Holloway, P. H.; Sun, S.-S.; and Tuenge, R. T. "Materials used in electroluminescent displays." *MRS Bulletin* (1996) 21(3): 49-58.

Shirota, Y. Organic materials for electronic and optoelectronic devices. *Journal of Materials Chemistry*. (2000) 10(1): 1-25.

Tang, C. W.; and Van Slyke, S. A. Organic electroluminescent diodes. *Applied Physics Letters* (1987)51(12): 913-915.

Van Slyke, S. A.; Chen, C. H.; and Tang, C. W. Organic electroluminescent devices with improved stability. *Applied Physics Letters* (1996) 69(15): 2160-2162.

Wagner, H. J.; Loutfy, R. O.; and Hsiao, C. K. Purification and characterization of phthalocyanines. *Journal of Materials Science* (1982) 17(10): 2781-2791.

Wang, S.; Liu, A.; and Hassan, A. Luminescent Compounds and Methods of Making and Using Same. U.S. Pat. No. 6,312,835, issued on Nov. 6, 2001.

Wang, S.; Liu, A.; and Hassan, A. Luminescent Compounds and Methods of Making and Using Same. U.S. Pat. No. 6,500,569, issued Dec. 31, 2002.

Wu, Q.; Lavigne, J. A.; Tao, Y.; D'Iorio, M.; and Wang, S. (2001) Novel Blue Luminescent/Electroluminescent 7-Azaindole Derivatives: 1,3-Di(N-7-azaindolyl)benzene, 1-Bromo-3,5-Di(N-7-azaindolyl)benzene, 1,3,5-Tri(N-7-azaindolyl)benzene, and 4,4'-Di(N-7-azaindolyl)biphenyl. *Chemistry of Materials* (2001) 13(1): 71-77.

Yamazaki, S. Chromium(VI) oxide-catalyzed oxidation of arenes with periodic acid. *Tetrahedron Letters* (2001) 42(19): 3355-3357.

Yang, W.; Chen, L.; and Wang, S. Syntheses, Structures, and Luminescence of Novel Lanthanide Complexes of Tripyridylamine, N,N,N',N'-Tetra(2-pyridyl)-1,4-phenylenediamine, and N,N,N',N'-Tetra(2-pyridyl)-biphenyl-4,4'-diamine. *Inorganic Chemistry* (2001) 40: 507-515.

We claim:

1. A compound represented by formula (1)

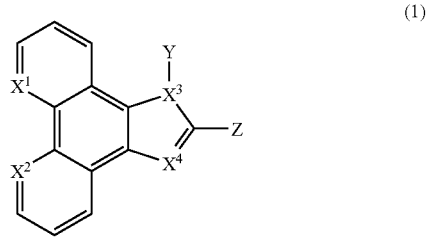

(1)

wherein X¹, X², X³ and X⁴ are nitrogen;
Y is selected from the group consisting of a substituted or unsubstituted aryl group, and a substituted or unsubstituted aliphatic group having 1-24 carbon atoms which may be straight, branched or cyclic;
Z is a substituted or unsubstituted aryl moiety selected from the group consisting of phenyl, biphenyl, naphthyl, anthryl, phenanthryl, pyrenyl, pyridyl, bipyridyl, indyl, and quinolinyl; and
wherein a said substituent is selected from the group consisting of an aryl group, an alkoxy group, a hydroxy group, a halo group, a nitro group, a nitrile group, —CF₃ and an aliphatic group having 1-24 carbon atoms which may be straight, branched or cyclic.

2. A compound as claimed in claim 1 wherein said compound is photoluminescent or electroluminescent.

3. A compound as claimed in claim 1 wherein Y is an aliphatic group having 1-12 carbon atoms.

4. A compound as claimed in claim 1 wherein Y is an aliphatic group having 1-4 carbon atoms.

5. A method of synthesizing a compound of formula

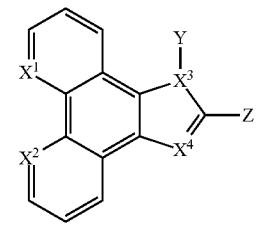

comprising at least one step selected from the group consisting of:

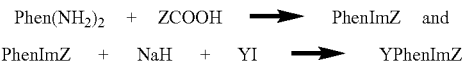

wherein PhenIm is imidazo[4,5-f]-[1,10]phenanthroline;
X¹, X², X³ and X⁴ are nitrogen;
Y is selected from the group consisting of substituted or unsubstituted aryl group, and substituted or unsubstituted aliphatic group having 1-24 carbon atoms which may be straight, branched or cyclic;
Z is selected from the group consisting of phenyl, biphenyl, naphthyl, anthryl, phenanthryl, pyrenyl, pyridyl, bipyridyl, indyl, and quinolinyl; and wherein a said substituent is selected from the group consisting of an aryl group, an alkoxy group, a hydroxy group, a halo group, a nitro group, a nitrile group, —CF$_3$ and an aliphatic group having 1-24 carbon atoms which may be straight, branched or cyclic.

6. A method of synthesizing a compound of formula

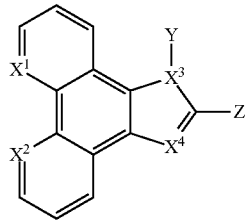

comprising at least one step selected from the group consisting of:

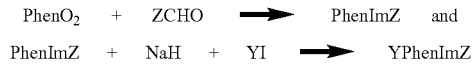

wherein PhenyIm is imidazo[4,5-f]-[1,10]phenanthroline; X$^1$, X$^2$, X$^3$ and X$^4$ are nitrogen;
Y is selected from the group consisting of substituted or unsubstituted aryl group, and substituted or unsubstituted aliphatic group having 1-24 carbon atoms which may be straight, branched or cyclic;
Z is selected from the group consisting of phenyl, biphenyl, naphthyl, anthryl, phenanthryl, and pyrenyl; and
wherein a said substituent is selected from the group consisting of an aryl group, an alkoxy group, a hydroxy group, a halo group, a nitro group, a nitrile group, —CF$_3$ and an aliphatic group having 1-24 carbon atoms which may be straight, branched or cyclic.

7. A photoluminescent or electroluminescent compound having a formula selected from the group consisting of 2-(9-anthryl)imidazo[4,5-f]-[1,10]phenanthroline (2), 1-methyl-2-(9-anthryl)imidazo[4,5f]-[1,10]phenanthroline (3), 2-(2-pyridyl)imidazo[4,5-f]-[1,10]-phenanthroline (4), and 1-methyl-2-(2-pyridyl)imidazo[4,5-f]-[1,10]-phenanthroline (5).

8. A composition comprising a compound as claimed in claim 1, an organic polymer and a solvent.

9. A composition comprising a photoluminescent or electroluminescent compound as claimed in claim 2, an organic polymer and a solvent.

10. A photoluminescent product or an electroluminescent product comprising a compound as claimed in claim 2 or claim 7.

11. The product of claim 10 which is a flat panel display device.

12. An electroluminescent device for use with an applied voltage, comprising:
a first electrode,
an emitter which is an electroluminescent compound as claimed in claim 2 or claim 7, and
a second, transparent electrode,
wherein voltage is applied to the two electrodes to produce an electric field across the emitter so that the emitter electroluminesces.

13. An electroluminescent device for use with an applied voltage, comprising:
a first electrode,
a second, transparent electrode,
an electron transport layer adjacent the first electrode,
a hole transport layer adjacent the second electrode, and
an emitter which is an electroluminescent compound as claimed in claim 2 or claim 7 interposed between the electron transport layer and the hole transport layer,
wherein voltage is applied to the two electrodes to produce an electric field across the emitter so that the emitter electroluminesces.

14. 2-(9-anthryl)imidazo[4,5-f]-[1,10]phenanthroline (2).
15. 1-methyl-2-(9-anthryl)imidazo[4,5-f]-[1,10]phenanthroline (3).
16. 2-(2-pyridyl)imidazo[4,5-f]-[1,10]phenanthroline (4).
17. 1-methyl-2-(2-pyridyl)imidazo[1,10]phenanthroline (5).
18. A compound represented by formula (1)

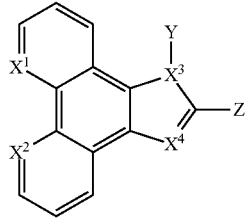

(1)

wherein X$^1$, X$^2$, X$^3$ and X$^4$ are nitrogen;
Y is selected from the group consisting of hydrogen, a substituted or unsubstituted aryl group, and a substituted or unsubstituted aliphatic group having 1-24 carbon atoms which may be straight, branched or cyclic;
Z is a substituted or unsubstituted aryl moiety selected from the group consisting of biphenyl, anthryl, phenanthryl, pyrenyl, pyridyl, bipyridyl, indyl, and quinolinyl; and
wherein a said substituent is selected from the group consisting of an aryl group, an alkoxy group, a hydroxy group, a halo group, an amino group, a nitro group, a nitrile group, —CF$_3$ and an aliphatic group having 1-24 carbon atoms which may be straight, branched or cyclic.

19. A compound as claimed in claim 18, wherein said compound is photoluminescent or electroluminescent.

20. A compound as claimed in claim 18, wherein Y is an aliphatic group having 1-12 carbon atoms.

21. A compound as claimed in claim 18, wherein Y is an aliphatic group having 1-4 carbon atoms.

22. A composition comprising a compound as claimed in claim 18, an organic polymer and a solvent.

23. A composition comprising a photoluminescent or electroluminescent compound as claimed in claim 19, an organic polymer and a solvent.

24. A photoluminescent product or an electroluminescent product comprising a compound as claimed in claim 19.

25. The product of claim 24 which is a flat panel display device.

26. An electroluminescent device for use with an applied voltage, comprising:
a first electrode,
an emitter which is an electroluminescent compound as claimed in claim 19, and
a second, transparent electrode, wherein voltage is applied to the two electrodes to produce an electric field across the emitter so that the emitter electroluminesces.

27. An electroluminescent device for use with an applied voltage, comprising:
a first electrode,
a second, transparent electrode,
an electron transport layer adjacent the first electrode,
a hole transport layer adjacent the second electrode, and
an emitter which is an electroluminescent compound as claimed in claim 19 interposed between the electron transport layer and the hole transport layer,
wherein voltage is applied to the two electrodes to produce an electric field across the emitter so that the emitter electroluminesces.

28. A method of synthesizing a compound of formula

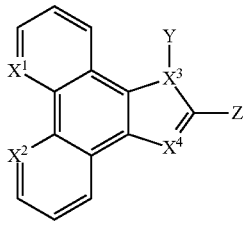

comprising at least one step selected from the group consisting of:

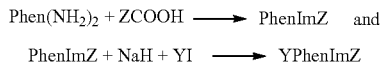

wherein PhenyIm is imidazo[4,5-f]-[1,10]phenanthroline; $X^1$, $X^2$, $X^3$ and $X^4$ are nitrogen;
Y is selected from the group consisting of hydrogen, substituted or unsubstituted aryl group, and substituted or unsubstituted aliphatic group having 1-24 carbon atoms which may be straight, branched or cyclic;
Z is selected from the group consisting of biphenyl, anthryl, phenanthryl, pyrenyl, pyridyl, bipyridyl, indyl, and quinolinyl; and
wherein a said substituent is selected from the group consisting of an aryl group, an alkoxy group, a hydroxy group, a halo group, an amino group, a nitro group, a nitrile group, —$CF_3$ and an aliphatic group having 1-24 carbon atoms which may be straight, branched or cyclic.

29. A method of synthesizing a compound of formula

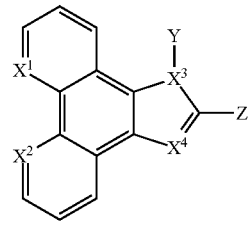

comprising at least one step selected from the group consisting of:

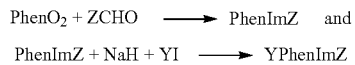

wherein PhenyIm is imidazo[4,5-f]-[1,10]phenanthroline; $X^1$, $X^2$, $X^3$ and $X^4$ are nitrogen;
Y is selected from the group consisting of hydrogen, substituted or unsubstituted aryl group, and substituted or unsubstituted aliphatic group having 1-24 carbon atoms which may be straight, branched or cyclic;
Z is selected from the group consisting of biphenyl, anthryl, phenanthryl, and pyrenyl; and
wherein a said substituent is selected from the group consisting of an aryl group, an alkoxy group, a hydroxy group, a halo group, an amino group, a nitro group, a nitrile group, —$CF_3$ and an aliphatic group having 1-24 carbon atoms which may be straight, branched or cyclic.

* * * * *